(12) United States Patent
Tyan et al.

(10) Patent No.: US 10,746,744 B2
(45) Date of Patent: Aug. 18, 2020

(54) METHODS OF DETECTING DONOR-SPECIFIC ANTIBODIES AND SYSTEMS FOR PRACTICING THE SAME

(71) Applicant: The Board of Trustees of the Leland Stanford Junior University, Stanford, CA (US)

(72) Inventors: Dolly B. Tyan, Palomar Park, CA (US); Ge Chen, Redwood City, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 55 days.

(21) Appl. No.: 16/109,481

(22) Filed: Aug. 22, 2018

(65) Prior Publication Data
US 2019/0079096 A1 Mar. 14, 2019

Related U.S. Application Data

(63) Continuation of application No. 14/775,150, filed as application No. PCT/US2014/026406 on Mar. 13, 2014, now Pat. No. 10,101,337.
(Continued)

(51) Int. Cl.
G01N 33/68 (2006.01)
G01N 33/543 (2006.01)
(Continued)

(52) U.S. Cl.
CPC ....... G01N 33/686 (2013.01); G01N 33/5091 (2013.01); G01N 33/5094 (2013.01);
(Continued)

(58) Field of Classification Search
CPC ............. G01N 33/686; G01N 33/5091; G01N 33/5094; G01N 33/54313;
(Continued)

(56) References Cited

U.S. PATENT DOCUMENTS 4,708,871 A 11/1987 Geysen
5,035,995 A 7/1991 Taguchi et al.
(Continued)

FOREIGN PATENT DOCUMENTS

CN 1423130 6/2003
CN 1444044 9/2003
(Continued)

OTHER PUBLICATIONS

Ahrens, et al. (2003) "Receptor-Mediated Endocytosis of Iron-Oxide Particles Provides Efficient Labeling of Dendritic Cells for In Vivo MR Imaging", Magnetic Resonance in Medicine 19:1006-1013.
(Continued)

*Primary Examiner* — Gailene Gabel
(74) *Attorney, Agent, or Firm* — Edward J. Baba; Bozicevic, Field & Francis LLP

(57) ABSTRACT

Provided are methods for determining the presence or absence of donor specific antibodies in a biological sample. The methods include mixing a cellular sample from a donor with a biological sample from a recipient under conditions sufficient for recipient immune antibodies, if present, to bind to donor cell surface antigen (Ag) to form an immune antibody-Ag complex, contacting the mixture with beads comprising an antibody that specifically binds the immune antibody-Ag complex (e.g., the Ag or immune antibody) on a surface thereof, adding under lysis conditions a detectably-labeled antibody that specifically binds the immune antibody-Ag complex bound to the beads, and detecting the presence or absence of the detectably-labeled antibody bound to the immune antibody-Ag complex to determine the presence or absence of donor specific antibodies in the biological sample from the recipient. Systems and kits for practicing the subject methods are also provided.

11 Claims, 19 Drawing Sheets

Related U.S. Application Data

(60) Provisional application No. 61/782,003, filed on Mar. 14, 2013.

(51) Int. Cl.
  *G01N 33/50* (2006.01)
  *G01N 33/569* (2006.01)
  *G01N 33/58* (2006.01)

(52) U.S. Cl.
  CPC . G01N 33/54313 (2013.01); G01N 33/54333 (2013.01); G01N 33/56977 (2013.01); G01N 33/582 (2013.01); G01N 33/6854 (2013.01); *G01N 2333/4716* (2013.01)

(58) Field of Classification Search
  CPC ....... G01N 33/54333; G01N 33/56977; G01N 33/582; G01N 33/6854; G01N 2333/4716
  See application file for complete search history.

(56) References Cited

U.S. PATENT DOCUMENTS

| | | | |
|---|---|---|---|
| 5,223,397 | A | 6/1993 | Pouletty |
| 5,270,169 | A | 12/1993 | Chang et al. |
| 5,851,829 | A | 12/1998 | Marasco et al. |
| 5,965,371 | A | 10/1999 | Marasco et al. |
| 6,146,589 | A | 11/2000 | Chandler |
| 6,150,122 | A | 11/2000 | Lee et al. |
| 6,159,748 | A | 12/2000 | Hechinger |
| 6,514,714 | B1 | 2/2003 | Lee et al. |
| 7,332,349 | B2 * | 2/2008 | Yang ............... G01N 33/5432 435/173.4 |
| 8,828,664 | B2 * | 9/2014 | Fekete ............. C12N 15/1003 435/6.12 |
| 2005/0059095 | A1 | 3/2005 | Yang et al. |
| 2005/0277158 | A1 * | 12/2005 | Chen ................ G01N 33/564 435/7.2 |
| 2005/0282172 | A1 | 12/2005 | Liu |
| 2007/0042414 | A1 | 2/2007 | Hutchens et al. |
| 2007/0042505 | A1 | 2/2007 | Israel et al. |
| 2009/0075378 | A1 | 3/2009 | Horlick et al. |
| 2011/0281757 | A1 * | 11/2011 | Tyan ................ G01N 33/543 506/9 |
| 2012/0070834 | A1 | 3/2012 | Greinacher et al. |
| 2012/0065092 | A1 | 5/2012 | Wai et al. |
| 2015/0240229 | A1 | 8/2015 | Gjerde |
| 2016/0033524 | A1 | 2/2016 | Tyan et al. |
| 2016/0041185 | A1 | 2/2016 | Tyan et al. |
| 2018/0052154 | A1 | 2/2018 | Stoner et al. |

FOREIGN PATENT DOCUMENTS

| | | |
|---|---|---|
| CN | 1766616 | 5/2006 |
| EP | 0204522 | 12/1986 |
| JP | 61245060 | 10/1986 |
| JP | 63109371 | 5/1988 |
| JP | A501571 | 6/1989 |
| JP | TH06508687 | 9/1994 |
| JP | 2001521909 | 11/2001 |
| JP | 2008100986 | 5/2008 |
| JP | A2009080019 | 4/2009 |
| WO | WO2008035047 | 3/2008 |
| WO | WO2010138456 | 12/2010 |
| WO | WO2013029181 | 3/2013 |

OTHER PUBLICATIONS

Kempf et al. (2003) "Improved Stimulation of Human Dendritic Cells by Receptor Engagement with Surface-modified Microparticles", Journal of Drug Testing 11(1):11-18.

Lewis, et al. (2012) "Microparticle Surface Modifidations Targeting Dendritic Cells for Non-Activiating Applications", Biomaterials 33:7221-7232.

Schønau, et al. (1998) "A One-Step Solid Phase Immunoassay for Simultaneous Detection of Serum IgG and IgM Antibodies to Borrelia Burgdorferi", Journal of Immunological Methods 218.1-2 :9-17.

Anjaneyulu & Staros (1987) "Reactions of N-Hydroxysulfosuccinimide Active Esters" *Int. J. Pept. Protein Res.* 30(1):117-124.

Billen et al. (2008) "Luminex donor-specific crossmatches" Tissue antigens 71(6):507-513.

Brinkley (1992) "A Brief Survey of Methods for Preparing Protein Conjugates with Dyes, Haptens, and Cross-Linking Reagents" *Bioconjug. Chem.* 3(1):2-13.

Chen et al. (2011) "Novel C1q assay reveals a clinically relevant subset of human Leukocyte antigen antibodies independent of immunoglobulin G strength on single antigen beads" *Hum. Immunol.* 72(10):849-858.

Chen et al. (2013) "C1q Assay for the Detection of Complement Fixing Antibody to HLA Antigens" Methods in Molecular Biology 1034:305-311.

Elshal & McCoy (2006) "Multiplex Bead Array Assays: Performance Evaluation and Comparison of Sensitivity to ELISA" Methods, 38(4):317-323.

Geysen et al. (1986) "A priori Delineation of a Peptide Which Mimics a Discontinuous Antigenic Determinant" *Mol. Immunol.* 23(7):709-715.

Geysen et al. (1984) "Use of Peptide Synthesis to Probe Viral Antigens for Epitopes to a Resolution of a Single Amino Acid" *Proc. Natl. Acad. Sci. USA* 81(13):3998-4002.

Hashida et al. (1984) "More Useful Maleimide Compounds for the Conjugation of Fab' to Horseradish Peroxidase through Thiol Groups in the Hinge" *J. Appl. Biochem.* 6(1-2):56-63.

International Search Report for PCT Appln No. PCT/US2009/065984 datd Mar. 30, 2010.

Kishore et al., (1997) "Release of calreticulin from neutrophils may alter C1q-mediated immune functions" Biochem J 322(pt 2):543-550.

Kishore et al., (2003) "Modular Organization of the Carboxyl-Terminal, Globular Head Region of Human C1q A, B, and C Chains" Journal of Immunology, 171(2):812-820.

Kishore et al. (2004) "C1q and Tumor Necrosis Factor Superfamily: Modularity and Versatility" *Trends Immunol.* 25(10):551-561.

Pei et al. (1998) "Simultaneous HLA Class I and Class II antibodies screening with flow cytometry" *Human Immunology* 59(5):313-322.

Smith et al. (1994) "β-Sheet Secondary Structure of the Trimeric Globular Domain of C1q of Complement and Collagen Types VIII and X by Fourier-Transform Infrared Spectroscopy and Averaged Structure Predictions" *Biochem. J.* 301(Pt 1):249-256.

Smith et al. (2007) "C4d Fixing, Luminex Binding Antibodies—A New Tool for Prediction of Graft Failure after Heart Transplantation" *Am. J. Transplant.* 7(12):2809-2815.

Saunkratay et al. (1999) "Mechanism of complement-dependent haemolysis via the lectin pathway: role of the complement regulatory proteins" *Clin Exp Immunol* 117:442-448.

Steinberger et al. (2002) "Identification of human CD93 as the phagocytic C1q receptor (C1qRp) by expression cloning" *Journal of Leukocyte Biology*, 71:133-140.

Wahrmann et al. (2003) "Flow Cytometry Based Detection of HLA Alloantibody Mediated Classical Complement Activation" *J. Immunol. Methods.* 275(1/2):149-160.

Wahrmann et al. (2005) "[C4d]FlowPRA Screening—A Specific Assay for Selective Detection of Competent-Activating Anti-HLA Alloantibodies," *Hum. Immunol.* 66(5):526-534.

Yabu et al., (2011) "C1q-fixing human leukocyte antigen antibodies are specific for predicting transplant glomerulopathy and late graft failure after kidney transplant" Transplantation, 91(3):342-347.

\* cited by examiner

FIG. 2
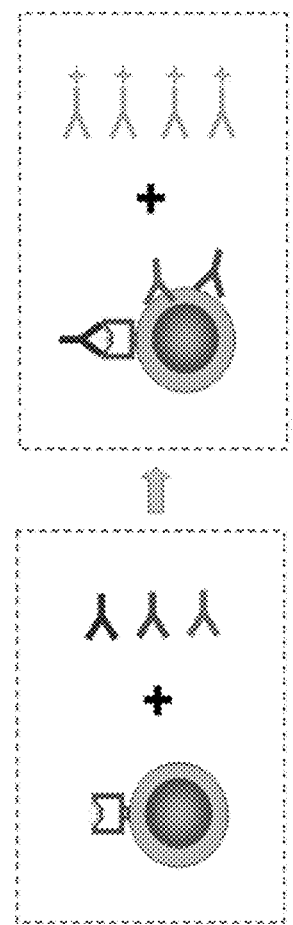
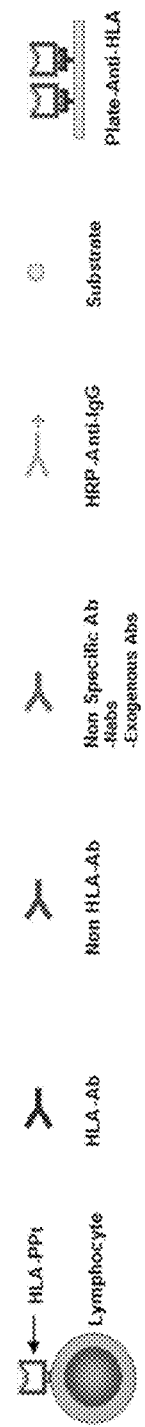

FIG. 5

SENSITIVITY COMPARISON
(Cell Number Titration; HLA-Ab C-I and II)

FIG. 6

| NO | CELL & TYPE | SERUM | DSA-FXM (MCS) | | LMX-IgG DSA |
|---|---|---|---|---|---|
| | | | HLA-CI | HLA-CII | (MFI) |
| 1 | | MX-BP | 81 | 135 | DP8-227 |
| 2 | CELL 17C-M:X1 A2,11;B27,35;Bw4,Bw6;Cw1,w4;DR1,DR8,DQ4,5 | MX-BP | 87 | 686 | A2-800-795, A5-345, B35-458, DR6-5556 |
| 3 | | MX-BP | 993 | 3 | B35-8888 |
| 4 | | MX-BP | 425 | 14 | A2-3333-8778 |
| 5 | | MX-BP | 102 | 77 | DR52-335 |
| 6 | CELL 18C-MX1: A2,28;B44,51;Bw4;Cw7,w14;DR2,DR11,DR52,53;DQ2,7 | MX-BP | 548 | 687 | A24-20555, A0-456-755, B35-448, DR4-273-3855, DR5-2055, 5555 |
| 7 | | MX-BP | 538 | 4 | A28-955, B51-8825-9950 |
| 8 | | MX-BP | 485 | 4 | A2-5733-8278 |
| 9 | CELL 11C-MX2: A24;B60;Bw6;Cw7;DR15,DR16,DR51;DQ5,6 | MX-BP | 866 | 723 | A24-2333, DR4-1525-8857-22348, DR8-C736-18857, DR5-9820-9807, DQ6-4456-2878 |
| 10 | | MX-BP | 22 | 29 | None |
| 11 | CELL 12C-MX2: A0,32;B7,B35;Bw4,Bw6;Cw7,w12;DR8,DR15,DR51;DQ6 | MX-BP | 887 | 842 | A2-9573-15442, A32-3407, DR4-3255, DR6-8807-22348, DR5-9820-9807, DQ6-4456-2878 |
| 12 | | MX-BP | -1 | 48 | None |
| 13 | | MX-BP | 485 | 755 | A2-1234-493, B44-5573-2255, Bw4-2758-15944, C3M-9646, 2554, DR50-4560-5745, DQ7-4570-794 |
| 14 | CELL 5C-MX1: A2,11; B7,44; BW4,BW6; CW5,10; DR4,15;DR51,53; DQ6,7 | MX-BP | -3 | -1 | None |
| 15 | | MX-BP | 873 | 531 | A0-9004-4509, B7-35552, DR8-8225-5905, DR50-9820-4750, DQ6-M30-20855 |
| 16 | | MX-BP | 552 | 195 | A0-9084-99955, B44-29425-23472, C8M-6525-30554, DR4-595, 73F |
| 17 | | MX-BP | 552 | 271 | A23-9807, A24-10055-9955, B44-9573-2255, Bw4-2758-15944, DQ3-3455-3355, DQ7-4570-794 |
| 18 | CELL 8C-MX1: A23,24; B39,44; Bw4,Bw6; CW4,7; DR14,17;DR52; DQ2,7;DPB1*0301,0402 | MX-BP | 8 | 121 | None |
| 19 | | MX-BP | 116 | 861 | A23-1957, A24-10055-200, B39-355, DP4-205-291 |
| 20 | | MX-BP | 534 | 467 | B44-29425, 23472, DQ2-9555, 18448 |
| 21 | CELL 2C-MX2: A2,24;B44;Bw4;Cw5,16;DR7;DR53;DQ2,9 | MX-BP | 446 | 623 | A2-205-1755, B44-9573-2255, DR7-5555, DR50-4245-C343, DQ9-2355-8877 |
| 22 | | MX-BP | 82 | 491 | A2-3247, 4725, DR7-1255, DQ3-2557, 17544, DQ4-1234,DQ8-8250-1250-554 |
| 23 | CELL 4C-MX2: A2,24; B39,41; Bw6; Cw7,17;DR8,12;DR52; DQ4,8 | MX-BP | 75 | 22 | A2-355-455,DQ4-85 |
| 23 | | MX-BP | 288 | 782 | A2-3247-4225, B39-4720, DR8-1984, DR9-9898, DR52-4277-9554 |

Cutoffs: LMX-IgG (MFI): HLA-CI/CII ≥ 1000
DSA-FXM (MCS): HLA-CI ≥ 61; HLA-CII ≥ 60

FIG. 7
DSA-FXM RESULT (DSA: HLA-DQ)

| NO | LMX-IgG DSA (MFI) | CELL | CELL HLA TYPE | SERUM | DSA-FXM (MCS) | |
|---|---|---|---|---|---|---|
| | | | | | HLA-CI | HLA-CII |
| 1 | B44, 20423, 2147?, DQ2, 10663, 14441 | 6C-MM1 | A2,24, B 39, 44, Bw4,Bw6, Cw4,?, DR4,??,DR52, DQ2,7 | MX1-84P | 634 | 467 |
| 2 | DQB1*0301, 6706, DQB1*0302, 234-1885, DQB1*0303, 292-85359 | YR | A3,31, B35, 46,Bw6, Cw4,3, DR8,01,3,DR53 DR51,0303,DR54 ?805,800,DDR81 03, 03 | HM | 22 | 286 |
| 3 | DQ4 4809, 3723 | CP | A3,24, B72,x Bw6, C?09, 10, DR55, DQ4, 6, DR51,6 | PS | 50 | 309 |
| 4 | DQB1*0501, 5528 DQB1*0502, 4601 | CC | A*0901,0201, B*0702,X Bw4, Cw*0702,X Bw6 Cw*0702,X, DR81*0801, ?55, DR52, DRB1*0801,0402.0024 | BC | ? | 120 |
| 5 | DQB1*0601, 4617, DQB1*0502, 891 | CP | A*0901,2402, B*0702,X Bw6 Cw*0702,X B8w4,Cw*0702,X, DR81*0801, ?58, DR52, DQB1*0602, 0602, DQA1 0102, 04,03902, DR81 0401, 0401 | CW | 14 | 197 |
| 6 | B*1302, 4639, DQB1*0601, 4136, DQB1*0602, 1777 | MF | A*2501,3501, B*1302, 3801,8w4, Cw*0602, 0203, DRB1*0403,1301, DRS2,53,DQB1*0301 0305, 0603, DRB1*0203,0401 | BC | 102 | 109 |
| 7 | B87, 708, 239, DQ2?, 1?309,16963, ,3651, 2437, 1510, | MR | A1,68 B51 B57 Bw4 DR8 DR11 DQ7,X | SB | 93 | 136 |

Cutoffs: LMX-IgG (MFI): HLA-CI/CII ≥ 1000  
DSA-FXM (MCS): HLA-CI ≥ 61; HLA-CII ≥ 68

FIG. 8

DSA-FXM RESULT (DSA: HLA-DP)

| NO | LMX-IgG DSA (MFI) | CELL | CELL HLA TYPE | SERUM | DSA-FXM (MCS) | |
|----|---|---|---|---|---|---|
| | | | | | HLA-CI | HLA-CII |
| 1 | DPB1*0301: 2023 | RK | A*0101,0201,B*0702,0801,Bw6, Cw*0701,0702, DPB1*0301,0501, DPB1*52, DQB1*0201, 0302,DPB1*0301,0401 | MD-1 | 36 | 249 |
| 2 | DPB1*0301: 3315 | CC | A*0201,0201,B*0702,X, Cw*0702,X,Bw4, DPB1*0301,0501, DQB1*0301, X,DPB1*0301,0402/0302N | MD-2 | 51 | 283 |
| 3 | A2-246,DPB1*0301: 13655; DP(C1q): 7448 | CC | A*0201,0201,B*0702,X, Cw*0702,X,Bw6, DPB1*0301,0501, DQB1*0301, X,DPB1*0301,0402/0302N | MD-3 | 226 | 656 |
| 4 | A*0206-246,DQB1*0301: 727; DPB1*0301: 11833 | FG | A*0201,2402,E*5602,5401Bw4,X,Bw4, Cw*0802,0702, DPB1*0405,1602, DPB1,DPB1,DQB1*0301, 0302,DPB1*0301X | MD-4 | 279 | 663 |
| 5 | A23-1987, A24-2460-3012, B39-1256; DP4-2085-3111 | 6C-MX1 | A2,24 B39,44, B*4,Bw6, Cw4,7, DPB4,17,DPB2, DQ2,7,DPB1*0301, 0402 | MX | 111 | 161 |
| 6 | C-I: Multi-Spec C-II: DP01: 1965 | CC | A*0101, 0201, E*0702, X, Bw6, Cw*0702,X,DPB1*0301, 0501, DQB1*0501, X, DPB1*0301,0402/0302N | BU | 602 | 115 |

Cutoffs: LMX-IgG (MFI): HLA-CI/CII ≥ 1000
DSA-FXM (MCS): HLA-CI ≥ 61; HLA-CII ≥ 60

FIG. 9

DSA-FXM RESULT (DSA: HLA-Cw)

| NO | LMX-IgG DSA (MFI) | CELL | CELL HLA TYPE | SERUM | DSA-FXM (MCS) HLA-CI | DSA-FXM (MCS) HLA-CII |
|---|---|---|---|---|---|---|
| 1 | Cw*0102: 2665; DRB1*0404: 3561; DRB1*0401:3436,DRB1*0405: 1946,DRB1*0502:2472 | FG | A*0201, A402, B*3502, 5401, B*41.X, Cw*0102,0702, DRB1*0405,X02, DPB1X03, DQB1*0401,0502, DPB1*0501X | VV | 243 | 346 |
| 2 | Cw6: 2173; DR51: 449; DPB1*0101:342 | HT | A*74.X, B*15.53, Cw*06.X, 8×4, DRB1*10X, C3×2, DR51, DQB1*03, X,DPB1*0101,0301/24 | HJ | 202 | 149 |
| 3 | Cw*0702: 4791 | RK | A*0301, 0204, B*0702, 0801,35×4, Cw*0701, 0702, DRB1*03:01,15:01, DR51:02, DQB1*0201, 0602,DPB1*03:01:0401 | JO | 249 | 38 |

Cutoff: LMX-IgG (MFI): HLA-CI/CII ≥ 1000
DSA-FXM (MCS): HLA-CI: ≥ 61; HLA-CII ≥ 60

FIG. 12

| SERUM DILUTION | FXM (MCS) | | DSA-FXM (MCS) | | LMX-DSA (MFI) (HLA-B7) |
|---|---|---|---|---|---|
| | Tc | Bc | CI | CII | |
| Neat | *404 | *423 | *681 | 17 | *10455 |
| 1:10 | *194 | *229 | *397 | 33 | *3288 |
| 1:25 | *112 | *128 | *288 | 9 | *1338 |
| 1:50 | 64 | 55 | *214 | 15 | **688 |
| 1:100 | 33 | 9 | *162 | -10 | 359 |
| 1:500 | 0 | -1 | 37 | -6 | 82 |
| 1:1000 | -3 | 1 | 12 | 5 | 23 |

CELLS: A3,24; B7,X; Bw6; DR8, 15; DR51; DQ4, 6; DPB1,6

*Positive; **Possible Positive

FIG. 13

| SERUM DILUTION | FXM (MCS) | | DSA-FXM (MCS) | | LMX-DSA (MFI) (HLA-DR4) |
|---|---|---|---|---|---|
| | Tc | Bc | CI | CII | |
| NEAT | 9 | *340 | *166 | *741 | *1369, *2473, *2188, *9559, *8646 |
| 1:100 | 6 | *199 | -10 | *356 | *1447, *1440, 1413, *1049, **847 |
| 1:500 | 4 | 42 | -44 | *158 | 253, 232, 227, 188, 114 |
| 1:1000 | 3 | -3 | -43 | *94 | 15, 12, 12, 11, 10 |

CELLS: A1, X; B35, 51; Bw4, Bw6; Cw*08, *15; DR*04BXRC, DR*1114; DR3*02YE; DR4*01DWH; DQ*0302, DQ*03;

DRB1*04:01, *04:02, *04:03, *04:04, *04:05

*Positive; **Possible Positive

| CI DSA | LMX-IgG DSA | |
|---|---|---|
| | + | − |
| DSA-FXM + | 52 | 5 |
| DSA-FXM − | 3 | 35 |

Concordance: 92%
P<0.0001
N=95

B

| CII DSA | LMX-IgG DSA | |
|---|---|---|
| | + | − |
| DSA-FXM + | 49 | 7 |
| DSA-FXM − | 2 | 42 |

Concordance: 91%
P<0.0001
N=100

C

DSA-FXM vs. LMX-IgG DSA

| DSA | CI | CII |
|---|---|---|
| SENSITIVITY | 95% | 96% |
| SPECIFICITY | 88% | 86% |

| NO | LMX-IgG DSA (MFI) | LMX-C1q DSA (MFI) | CELL HLA TYPE | FXM (CS) Tc | FXM (CS) Bc | DSA-FXM (CS) I | DSA-FXM (CS) II |
|---|---|---|---|---|---|---|---|
| 1 | A*0203: 10782 | Negative | A*0203,2402;B*3502,5401;Bw4,6;Cw*0702,0702; DRB1*0405,1502;DR51,53;DQB1*0401,0503;DPB1*0501,X | 40 | 1 | 20 | 14 |
| 2 | B*0801: 10426 | Negative | A*0101,0301;B*0703,0801;Bw6;Cw*0701,0702; DRB1*0301,1501;DR51,52;DQB1*0201,0602; DPB1*0201,0401 | 19 | 35 | 3 | 0 |
| 3 | | Negative | A*0201,3201;B*0801,4402;Bw4,6 Cw*0501,07; DRB1*0301,1501;DR51,52;DQB1*0201,0602; DPB1*0301,2601 | 10 | 4 | 23 | 24 |
| 4 | A*0201: 5851 | A*0201: 2889 | A*0201,3201;B*0801,4402;Bw4,6 Cw*0501,07; DRB1*0301,1501;DR51,52;DQB1*0201,0602; DPA1*0102/01,X | 17 | -3 | 23 | -7 |
| 5 | Cw*0501: 9520 | Cw*0501: 1738 | A*0101,0301;B*0702,3701;Bw4,6 Cw*0602,0702; DRB1*1501,X;DR51;DQ*0602,X;DPB1*0201,0401; DPA1*0102/01,X | -1 | 4 | 14 | 16 |
| 6 | DPB1*0401: 8269 | Negative | A*0101,0301;B*0702,X;Cw*0702,X;Bw6; DRB1*0101,0103;DQ*0501,X;DPB1*0101,0401/0332/01 | 61 | -7 | 44 | 20 |
| 7 | DQB1*0201: 427-1728 DPB1*0401: 8269 | Negative | A*0101,0301;B*0703,0801;Bw6; Cw*0701,0702; DRB1*0301,1501;DR51,DR52; DQ*0201, 0602;DPB1*0301,0401 | 46 | 7 | 34 | 15 |

FIG. 16

| CASE | LMX-IgG DSA (MFI) | Cells | Serum & Date | IgG-FXM (BCS) | | | | DL-FXM (BCS) | | | |
|---|---|---|---|---|---|---|---|---|---|---|---|
| | | | | TXM | BXM | Test Date | CI | CIIa | CIIb | Test Date |
| 1 | A2-680-789; B27-1129-1210; DR1-959-1163 | 91708 | 89695 6-23-12 | 65 | 162 | 2/5/2013 | 190 | NA | 14 | 2/7/2013 |
| | | 91708 | 89695 1-29-13 | 66 | 122 | 2/5/2013 | 185 | NA | 12 | 2/7/2013 |
| 2 | Invalid LMX-IgG Result | AUTO | 92081 10-11-12 | 355 | 421 | 11/26/2012 | 278 | 179 | 191 | 5/9/2013 |
| | | AUTO | 92081 11-19-12 | 355 | 418 | 11/26/2012 | 267 | 160 | 191 | 5/9/2013 |
| | | 92549 | 92081 10-11-12 | 337 | 377 | 11/26/2012 | 297 | 170 | 151 | 5/9/2013 |
| | | 92549 | 92081 11-19-12 | 328 | 378 | 11/26/2012 | 297 | 159 | 143 | 5/9/2013 |
| 3 | Cw*07:02-897; DRB1*04:03-940 | 95532 | 84237 3-26-13 | NA | NA | NA | -36 | 3 | 95 | 10/15/2013 |
| | Cw*07:02-428; DRB1*04:03-898 | 95532 | 84237 6-18-13 | -8 | 140 | 6/25/2013 | -41 | -11 | 83 | 10/15/2013 |
| 4 | | Auto | 97819 12-03-13 | 228 | 239 | 10/13/2012 | 218 | No cells available | | |
| | Cw8-3403 | 97968 | 97819 12-03-13 | 224 | 228 | 2012/20/13 | | -5 | -38 | 2/10/2014 |

FIG. 17
DSA-FXM CI
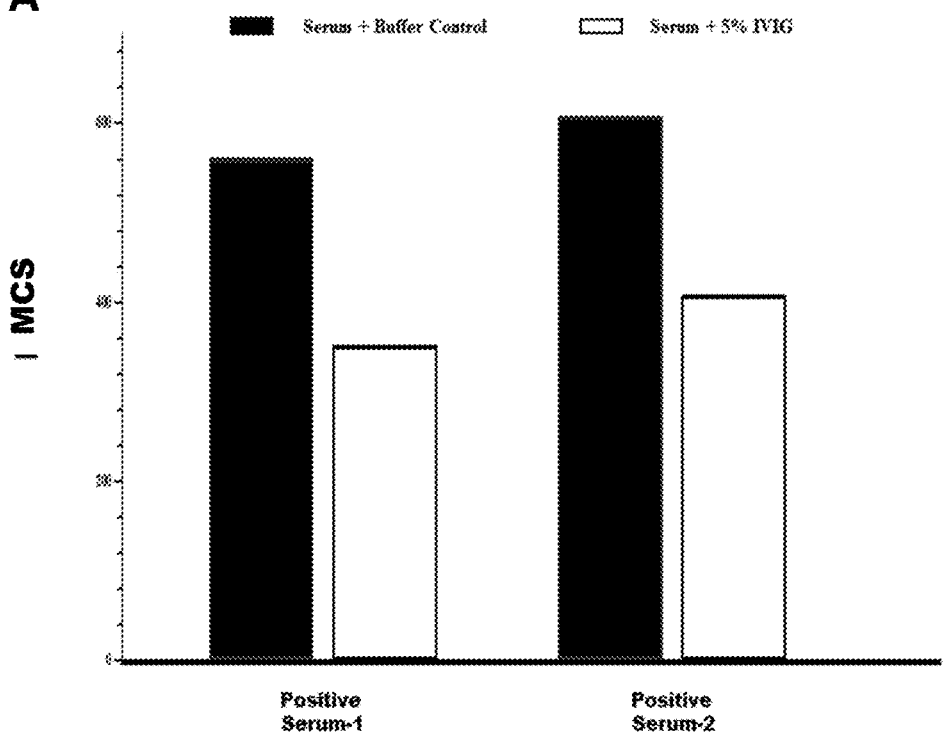
DSA-FXM CII
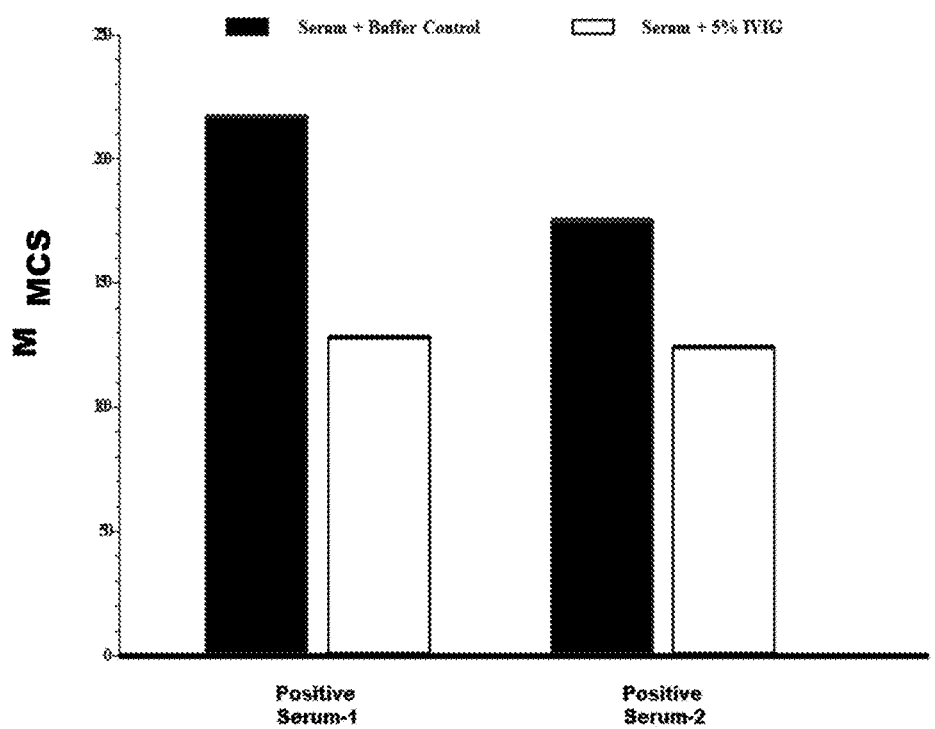

FIG. 18
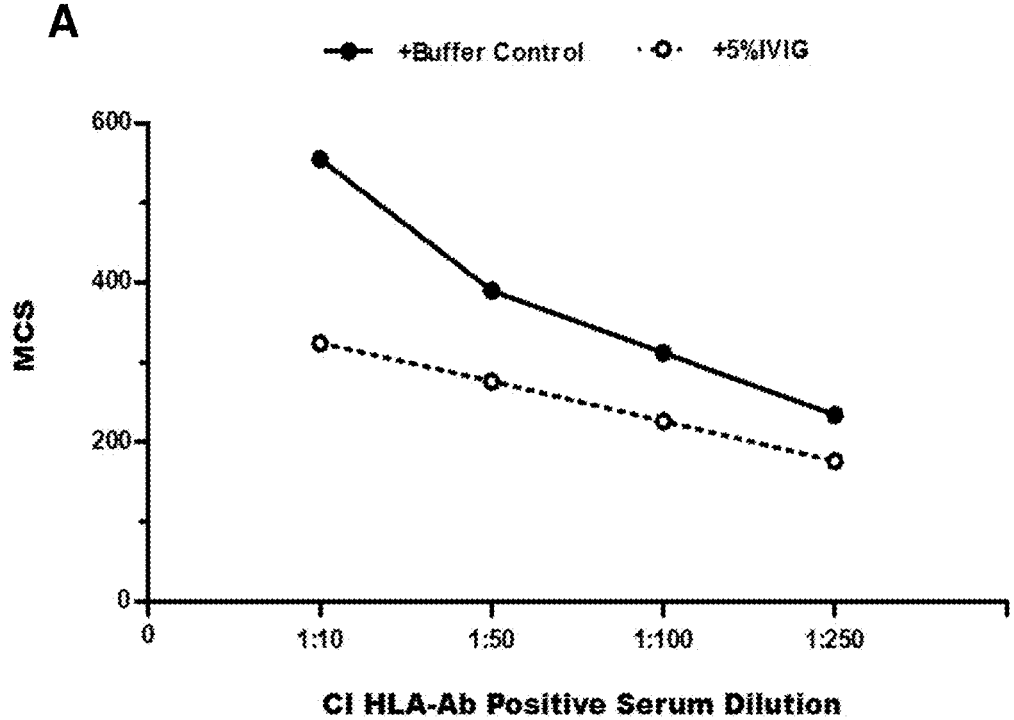
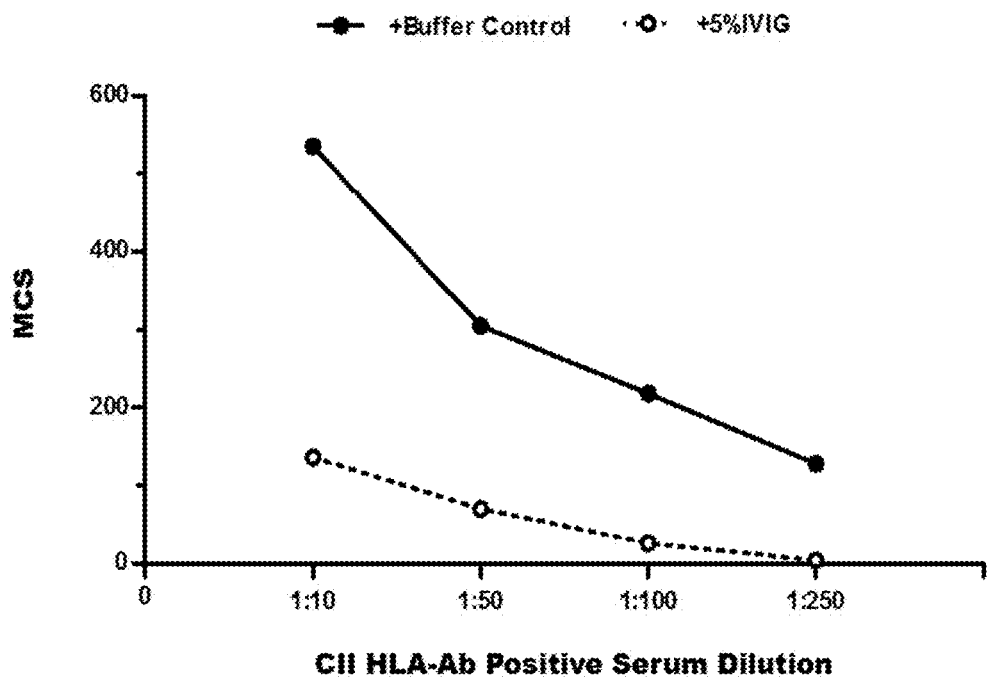

METHODS OF DETECTING DONOR-SPECIFIC ANTIBODIES AND SYSTEMS FOR PRACTICING THE SAME

CROSS-REFERENCE TO RELATED APPLICATIONS

This application is a continuation of U.S. patent application Ser. No. 14/775,150, filed Sep. 11, 2015, issued as U.S. Pat. No. 10,101,337, which application is a 371 of PCT/US2014/026406, filed Mar. 13, 2014, which application claims the benefit of U.S. Provisional Patent Application Ser. No. 61/782,003, filed Mar. 14, 2013, the disclosure of which is incorporated herein by reference in its entirety.

BACKGROUND

Over 100,000 solid organ transplants are performed annually worldwide, including tens of thousands performed annually in the United States. Despite significant improvements in immunosuppression and post-transplant care, long term graft function is less than optimal. In the United States, adjusted 10 year allograft survival rates for deceased and living donor kidney transplants are only about 40% and 60%, respectively. Early and late stage graft failure, secondary to antibody mediated rejection (AMR) is a significant cause of poor graft survival.

Antibodies to Human Leukocyte Antigens (HLA) are circulating antibodies present in the transplant candidate or recipient's blood which are the result of an earlier sensitization event (blood transfusion, previous transplant, or pregnancy). Donor specific antibodies (DSA) present pre-transplant can cause hyper-acute rejection and immediate graft loss and are assessed by a pre-transplant crossmatch. In more recent years, the concept of monitoring for the post-transplant development of clinically relevant antibodies directed against donor specific HLA class I and class II mismatches has been a significant area of interest within the transplant community. Whether detected pre- or post-transplant, the presence of antibodies directed against antigens expressed on donor organs, when not treated clinically, results in an immune attack on the transplanted organ, and increases risk of graft loss and/or rejection. DSA attacks, among others, the endothelium of the allograft, and can result in subsequent biopsy proven AMR and acute injury requiring augmented immunosuppression. The progression of DSA development and the corresponding clinical events compound to damage the allograft, resulting in chronic changes over time that ultimately compromise graft function and survival.

Antibody mediated rejection can present as an early acute process, resulting from an anamnestic response or de novo antibody production, or as a late and chronic process due to de novo antibody production. In the acute phase, it is often preformed antibodies that cause early rejection, but de novo DSA can also develop in the early post-transplant period, resulting in acute rejection. Patients with preformed DSA are at significantly greater risk of having an acute AMR and have significantly lower graft survival.

Chronic rejection is one of the leading causes of death-censored graft loss. Repeated cycles of alloantibody-mediated injury and repair result in distinct changes in the microvasculature of the allograft. Patients with preformed DSA and those who develop de novo DSA are at an increased risk of having chronic rejection.

SUMMARY

Provided are methods for determining the presence or absence of donor specific antibodies in a biological sample. The methods include forming a mixture by combining a cellular sample from a donor with a biological sample from a recipient under conditions sufficient for recipient immune antibodies, if present, to bind to donor cell surface antigen (Ag) to form an immune antibody-Ag complex, contacting the mixture with beads comprising an antibody that specifically binds the immune antibody-Ag complex (e.g., the Ag or immune antibody) on a surface thereof, adding under lysis conditions a detectably-labeled antibody that specifically binds the immune antibody-Ag complex bound to the beads, and detecting the presence or absence of the detectably-labeled antibody bound to the immune antibody-Ag complex to determine the presence or absence of donor specific antibodies in the biological sample from the recipient. Systems and kits for practicing the subject methods are also provided.

BRIEF DESCRIPTION OF THE DRAWINGS

The invention may be best understood from the following detailed description when read in conjunction with the accompanying drawings. Included in the drawings are the following figures:

FIG. 2 schematically illustrates a method for determining the presence or absence of donor specific antibodies in a biological sample according to a second embodiment of the present disclosure.

FIG. 3, panel A: both HLA-Class I (C-I) and Class II (C-II) donor specific antibody (DSA) were negative (CI−/CII−); FIG. 3, panel B: only C-II DSA was positive (CI−/CII+); FIG. 3, panel C: only C-I DSA was positive (CI+/CII−); and FIG. 3, panel D: both CI and C-II DSAs were positive (CI+/CII+).

FIG. 5 provides results of a DSA-FXM experiment. A pool of HLA-Ab positive sera (PPS) in different dilutions was tested against various cell numbers by FXM, DSA-FXM, and LMX-IgG. The results show DSA-FXM is the most sensitive method for detecting DSA and uses many fewer cells (e.g. DSA can be detected with as few as 25,000 cells) when compared with standard methods. LMX-IgG defines the HLA specificities contained in the PPS serum on a Luminex platform using single antigen beads and the values shown are the mean fluorescence intensities (MFI). Values greater than or equal to 1000 MFI are considered positive; values between 500-999 MFI are considered possible positives (equivocal).

FIG. 6 shows results of a DSA-FXM experiment. Twenty-three CAP (the College of American Pathologists) external proficiency samples were tested by DSA-FXM simultaneously with the blinded challenge and in parallel with the regular flow cytometry crossmatch (FXM) and standard Luminex antibody screening on single antigen beads (LMX-IgG). The donor specific antibodies (DSAs) of HLA-class I (C-I) and/or HLA-II (C-II) were identified and most DSAs were further confirmed by LMX-IgG. Some extra DSA with low MCS were only detected with the more sensitive DSA-FXM method. External proficiency samples are sera and cells with known specificities. The specificities of the sera are blinded to the participants until all results are received from all participating centers.

FIG. 7 provides results of a DSA-FXM experiment. Seven HLA-DQ DSA positive samples were identified by LMX-IgG and confirmed by DSA-FXM. Historically, it has been impossible to detect all specific DSA to DQ by any kind of DSA assay involving cells or cell extracts.

FIG. 8 shows results of a DSA-FXM experiment. Six HLA-DP DSA positive samples were identified by LMX-IgG and confirmed by DSA-FXM.

FIG. 9 provides results of a DSA-FXM experiment. Three HLA-C DSA positive samples were identified by LMX-IgG and confirmed by DSA-FXM.

FIG. 12 shows a sensitivity comparison of FXM, DSA-FXM, and LMX-IgG single antigen bead assay for a class I specific DSA (B7), showing that DSA-FXM can detect specific HLA class I DSA on the target cell even when the other two tests are negative.

FIG. 13 shows a sensitivity comparison of FXM, DSA-FXM, and LMX-IgG single antigen bead assay for a class II specific DSA (DR4), showing that DSA-FXM can detect specific HLA class II DSA on the target cell even when the other two tests are negative.

FIG. 14 Panels A and B show the Pearson correlation between DSA-FXM and LMX-IgG SAB results for 95 class I DSA (Panel A) and 100 class II DSA (Panel B) FXM comparisons. Panel C shows sensitivity and specificity percentages for class I and II using IgG DSA as the standard. Panel D shows a comparison of LMX-IgG SAB, LMX-C1q SAB, FXM, and DSA-FXM on 7 serum samples (6 individuals). Discrepancies related to over-reactivity of the LMX-SAB. In conjunction with FIG. 15, results show that the LMX-IgG SAB give false positive reactions (i.e., DSA positive when both FXM and DSA-FXM are negative). This contributes to the lower specificity shown in FIG. 15.

FIG. 16 shows as comparison of the ability of FXM and DSA-FXM to distinguish positive reactions due to DSA class (I and/or II). DSA-FXM headers: CI beads detect all class I, CIIa detects DQ, CM detects all DR and DP but only some DQ. Shown are four different types of results. Cases 1 and 3 both have positive B cell FXMs, but Case 1 is due to class I alloantibody whereas Case 3 is due to Class II alloantibody. Cases 2 and 4 both have positive T and B FXMs, but Case 2 is due to autoantibody, whereas Case 4 is due to class I alloantibody.

FIG. 17 Panel A shows DSA-FXM results for class I DSA on serum diluted 1:2 in buffer and 1:2 in intravenous immunoglobulin (IVIG). IVIG is used for desensitization to HLA, to lower antibody. The usual FXM shows increases in the IVIG treated sample compared to buffer (data not shown) due to the presence of the second step anti-IgG reagent and broad reactivity of the IVIG with unknown targets on the cell surface. The DSA-FXM shows inhibition of the IVIG because the detection is specific to HLA. Thus the DSA-FXM reveals efficacy of treatment. Panel B shows DSA-FXM results for class II DSA on serum diluted 1:2 in buffer and 1:2 in intravenous immunoglobulin (IVIG). IVIG is used for desensitization to HLA, to lower antibody. The usual FXM shows increases in the IVIG treated sample compared to buffer (data not shown) due to the presence of the second step anti-IgG reagent and broad reactivity of the IVIG with unknown targets on the cell surface. The DSA-FXM shows inhibition of the IVIG because the detection is specific to HLA. Thus the DSA-FXM reveals efficacy of treatment.

FIG. 18 Panel A shows results of a positive DSA serum spiked with 5% IVIG and tested at different dilutions by DSA-FXM. Results showed that IVIG had a dose-dependent inhibition on both HLA class I DSAs. Panel B shows results of a positive DSA serum spiked with 5% IVIG and tested at different dilutions by DSA-FXM. Results showed that WIG had a dose-dependent inhibition on both HLA class II DSAs.

DEFINITIONS

Figure 1:
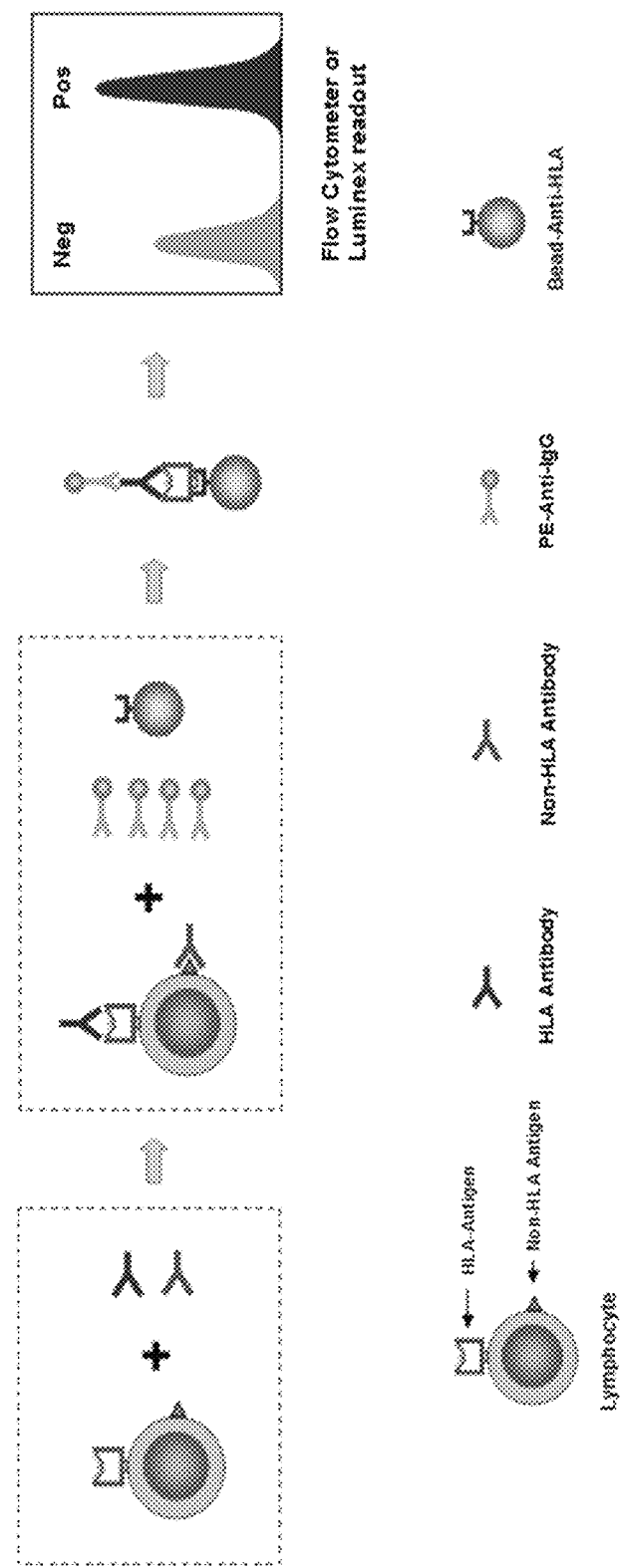
FIG. 1 schematically illustrates a method for determining the presence or absence of donor specific antibodies in a biological sample according to one embodiment of the present disclosure.

By "donor specific antibodies" or "DSAs" is meant antibodies present in a recipient that specifically bind to donor antigens (e.g., donor cell surface antigens). The DSAs may be "pre-formed" (e.g., present in the recipient prior to receiving a transplant or transfusion from a donor) and/or de novo DSAs which are produced by the recipient in response to having been pregnant, or receiving a transplant or transfusion from one or more donors. The DSAs can, in some cases, be autologous DSAs (autoantibodies) that bind to cell surface components of the recipient's own cells. In certain aspects, the DSAs are complement-fixing antibodies (CFAbs). In certain aspects, the DSAs are against HLA antigens.

An "affinity reagent" of the subject invention has an analyte binding domain, moiety, or component that has a high binding affinity for a target analyte. By high binding affinity is meant a binding affinity of at least about $10^{-4}$ M, usually at least about $10^{-6}$ M or higher, e.g., $10^{-9}$M or higher. The affinity reagent may be any of a variety of different types of molecules, so long as it exhibits the requisite binding affinity for the target protein when present as tagged affinity ligand.

As such, the affinity reagent may be a small molecule or large molecule ligand. By small molecule ligand is meant a ligand ranging in size from about 50 to about 10,000 daltons, usually from about 50 to about 5,000 daltons and more usually from about 100 to about 1000 daltons. By large molecule is meant a ligand in size from about 10,000 daltons or greater in molecular weight.

Of particular interest as large molecule affinity ligands are antibodies, as well as binding fragments and mimetics thereof. Where antibodies are the affinity ligand, they may be derived from polyclonal compositions, such that a heterogeneous population of antibodies differing by specificity are each tagged with the same tag. As such, the affinity ligand may be a monoclonal, oligoclonal, and/or polyclonal antibody. The affinity ligand may be an antibody binding fragment or mimetic, where these fragments and mimetics have the requisite binding affinity for the target protein. For example, antibody fragments, such as Fv, (Fab')$_2$, and Fab may be prepared by cleavage of the intact protein, e.g. by protease or chemical cleavage. Also of interest are recombinantly produced antibody fragments, such as single chain antibodies or scFvs, where such recombinantly produced antibody fragments retain the binding characteristics of the above antibodies. Such recombinantly produced antibody fragments generally include at least the VH and VL domains of the subject antibodies, so as to retain the binding characteristics of the subject antibodies. These recombinantly produced antibody fragments or mimetics of the subject invention may be readily prepared using any convenient methodology, such as the methodology disclosed in U.S. Pat. Nos. 5,851,829 and 5,965,371; the disclosures of which are herein incorporated by reference.

The above described antibodies, fragments and mimetics thereof may be obtained from commercial sources and/or prepared using any convenient technology, where methods of producing polyclonal antibodies, oligoclonal antibodies, monoclonal antibodies, fragments and mimetics thereof, including recombinant derivatives thereof, are known to those of skill in the art.

By "epitope" is meant a site on an antigen to which specific B cells and/or T cells respond. The term is also used interchangeably with "antigenic determinant" or "antigenic determinant site." An epitope can comprise 1 or more amino acids, such as three or more amino acids, in a spatial conformation unique to the epitope. An epitope may include from 1-10 amino acids, such as from 1-5 amino acids, e.g., 1, 2, 3, 4, or 5 amino acids. Methods of determining spatial conformation of amino acids are known in the art and include, for example, X-ray crystallography and 2-dimensional nuclear magnetic resonance. Furthermore, the identification of epitopes in a given protein is readily accomplished using techniques well known in the art. See, e.g., Geysen et al., Proc. Natl. Acad. Sci. USA (1984) 81:3998-4002 (general method of rapidly synthesizing peptides to determine the location of immunogenic epitopes in a given antigen); U.S. Pat. No. 4,708,871 (procedures for identifying and chemically synthesizing epitopes of antigens); and Geysen et al., Molecular Immunology (1986) 23:709-715 (technique for identifying peptides with high affinity for a given antibody). Antibodies that recognize the same epitope can be identified in a simple immunoassay showing the ability of one antibody to block the binding of another antibody to a target antigen.

By "binds specifically" or "specifically binds" is meant high avidity and/or high affinity binding of an antibody to a specific antigen or epitope. Antibody binding to its epitope on a specific antigen is with a greater avidity and/or affinity than binding of the same antibody to different epitopes, particularly different epitopes that may be present in molecules in association with, or in the same sample, as a specific antigen of interest. Complement fixing antibodies may, however, have the same or similar avidity and/or affinity for various epitopes on different antigens of interest. As such, "binds specifically" or "specifically binds" is not meant to preclude a given complement fixing antibody from binding to more than one antigen of interest. Antibodies that bind specifically to a polypeptide of interest may be capable of binding other polypeptides at a weak, yet detectable, level (e.g., 10% or less of the binding shown to the polypeptide of interest). Such weak binding, or background binding, is readily discernible from the specific antibody binding to the polypeptide of interest, e.g., by use of appropriate controls.

By "detectably-labeled" antibody is meant an antibody having an attached detectable label, where the antibody is capable of binding specifically to another molecule, e.g., another antibody (such as an IgG antibody). The detectably-labeled antibody retains binding specificity. The detectable label may be attached by chemical conjugation, or where the label is a polypeptide, it could be attached by genetic engineering techniques. Methods for production of detectably-labeled antibodies are well known in the art. Detectable labels may be selected from a variety of such labels known in the art, including radioisotopes, chromophores, fluorophores, fluorochromes, enzymes (e.g., horseradish peroxidase), linker molecules or other moieties or compounds which either emit a detectable signal (e.g., radioactivity, fluorescence, color) or emit a detectable signal after exposure of the label to its substrate. Various detectable label/substrate pairs (e.g., horseradish peroxidase/diaminobenzidine, biotin/streptavidin, luciferase/luciferin), methods for labeling antibodies, and methods for using labeled secondary antibodies to detect an antigen are well known in the art. See, e.g., Harlow and Lane, eds. (Using Antibodies: A Laboratory Manual (1999) Cold Spring Harbor Laboratory Press, Cold Spring Harbor, N.Y.).

By "isolated" is meant a compound of interest that is in an environment different from that in which the compound naturally occurs. "Isolated" is meant to include compounds that are within samples that are substantially enriched for the compound of interest and/or in which the compound of interest is partially or substantially purified. The term "isolated" encompasses instances in which compound is unaccompanied by at least some of the material with which it is normally associated in its natural state. For example, the term "isolated" with respect to a polypeptide generally refers to an amino acid molecule devoid, in whole or part, of sequences normally associated with it in nature; or a sequence, as it exists in nature, but having heterologous sequences in association therewith.

As used herein, "purified" means that the recited material comprises at least about 75% by weight of the total protein, with at least about 80% being preferred, and at least about 90% being particularly preferred. As used herein, the term "substantially pure" refers to a compound that is removed from its natural environment and is at least 60% free, preferably 75% free, and most preferably 90% free from other components with which it is naturally associated.

A "biological sample from a recipient" as used herein refers to a sample of tissue or fluid isolated from a recipient, which in the context of the invention generally refers to samples which may contain donor specific antibodies, which samples, after optional processing, can be analyzed in an in vitro assay. Samples of interest include, but are not limited to, blood, plasma, serum, blood cells, urine, saliva, biopsy tissue, and mucous. Samples also include samples of in vitro cell culture constituents including but not limited to conditioned media resulting from the growth of cells and tissues in culture medium, e.g., recombinant cells, and cell components.

By "human leukocyte antigen" or "HLA" is meant the genes within the major histocompatibility complex (MHC), which spans approximately 3.5 million base pairs on the short arm of chromosome 6. The MHC is divisible into 3 separate regions which contain the class I, the class II and the class III genes. In humans, the class I HLA complex is about 2000 kb long and contains about 20 loci. Within the class I region exist genes encoding the well characterized class I MHC molecules designated HLA-A, HLA-B and HLA-C. In addition, there are non-classical class I genes encoded by the HLA-E, HLA-F, HLA-G, HLA-H, HLA-J, HLA-X and MIC loci. The class II region contains six gene families encoded by the HLA-DRB1,3,4,5, HLA-DQA, HLA-DQB, and HLA-DPA, HLA-DPB loci. These genes encode the α and β chain of the classical class II MHC molecules designated HLA-DRB1, 3, 4, 5, DQ and DP. In humans, non-classical genes encoded by the DM, DN and DO loci have also been identified within class II. The class III region contains a heterogeneous collection of more than 36 loci associated with the immune response.

The terms "determining", "measuring", "evaluating", "assessing" and "assaying" are used interchangeably and include quantitative and qualitative determinations.

The term "solid substrate" refers to a solid support in which antigens and/or antibodies may be immobilized thereon. Exemplary solid substrates include multiwell plates, membranes including nitrocellulose membranes and polyethylene membranes, cell and cell membranes, beads, microparticles, microspheres, microbeads, and the like. The methods of the invention may be carried out with microparticles, microspheres, microbeads, or beads of any material, e.g. silica, gold, latex, polymers such as polystyrene, polysulfone, polyethyl, or hydrogel. In addition, the microparticles, microspheres, beads or microbeads may be a magnetic.

The term "complement fixing antibody" refers to an antibody that binds specifically to an antigen or a pathogen and initiates the complement cascade of the immune system that provides for clearance of the antigen bearing target (e.g., cell) or pathogen from the organism. In general, a complement fixing antibody is an IgM or an IgG antibody that is recognized and specifically bound by complement factor C1q, complement factor C3 via the alternate pathway, or the like.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

DETAILED DESCRIPTION

Provided are methods for determining the presence or absence of donor specific antibodies in a biological sample. The methods include forming a mixture by combining a cellular sample from a donor with a biological sample from a recipient under conditions sufficient for recipient immune antibodies, if present, to bind to donor cell surface antigen (Ag) to form an immune antibody-Ag complex, contacting the mixture with beads comprising an antibody that specifically binds the immune antibody-Ag complex (e.g., the Ag or immune antibody) on a surface thereof, adding under lysis conditions a detectably-labeled antibody that specifically binds the immune antibody-Ag complex bound to the beads, and detecting the presence or absence of the detectably-labeled antibody bound to the immune antibody-Ag complex to determine the presence or absence of donor specific antibodies in the biological sample from the recipient. Systems and kits for practicing the subject methods are also provided.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials may now be described. Any and all publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "an electrode" includes a plurality of such electrodes and reference to "the signal" includes reference to one or more signals, and so forth.

It is further noted that the claims may be drafted to exclude any element which may be optional. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. To the extent such publications may set out definitions of a term that conflict with the explicit or implicit definition of the present disclosure, the definition of the present disclosure controls.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

As summarized above, aspects of the invention include methods for determining the presence or absence of donor specific antibodies in a biological sample. The methods include forming a mixture by combining a cellular sample from a donor with a biological sample from a recipient under conditions sufficient for recipient immune antibodies, if present, to bind to donor cell surface antigen (Ag) to form an immune antibody-Ag complex, contacting the mixture with beads comprising an antibody that specifically binds the immune antibody-Ag complex (e.g., the Ag or immune antibody) on a surface thereof, adding under lysis conditions a detectably-labeled antibody that specifically binds the immune antibody-Ag complex bound to the beads, and detecting the presence or absence of the detectably-labeled antibody bound to the immune antibody-Ag complex to determine the presence or absence of donor specific antibodies in the biological sample from the recipient. Various steps and aspects of the methods will now be described in greater detail below.

By "donor" is meant a source (e.g., a human source) of the cellular sample. The donor may be different from the recipient (e.g., where the DSAs may be alloantibodies), or the donor and recipient may be the same (e.g., where the DSAs may be autoantibodies). In certain aspects, the donor may be a candidate for donating cells (e.g., blood cells), tissues (e.g., cornea, skin, bone, heart valve, tendon, femoral and/or saphenous veins, lymph nodes, spleen, and the like), organs (e.g., a kidney, heart, liver, pancreas, lung, intestine, eye, and the like), and any combinations thereof, to a recipient in need thereof. Donors of interest include human donors, non-human primate donors, mammalian donors (e.g., pigs), non-mammalian donors, and any other donor types of interest.

As used herein, a "cellular sample" from a donor is a sample obtained from the donor that includes at least one cell. The at least one cell may be a nucleated cell (e.g., a lymphocyte or peripheral blood mononuclear cell (PBMC)), or a cell lacking a nucleus (e.g., an erythrocyte or platelet). In certain aspects, the cellular sample is a sample obtained from the donor that includes cells selected from lymphocytes (e.g., T cells and/or B cells), PBMCs, erythrocytes, platelets, and any combination thereof. According to certain embodiments, the cellular sample from the donor is from a tissue of the donor (e.g., lymph nodes, spleen, cornea, skin, bone, heart valve, tendon, femoral and/or saphenous veins, and the like), from an organ of the donor (e.g., a kidney, heart, pancreas, lung, liver, intestine, eye, and the like), or any combination of such tissues and/or organs. The cellular sample may be subjected to a purification procedure prior to use in the methods of the present disclosure. For example, the cellular sample may be a substantially pure sample of lymphocytes, peripheral blood mononuclear cells (PBMCs), erythrocytes, and/or platelets, which sample is free of components that may interfere with the mixing, contacting and/or detecting steps of the subject methods. In certain aspects, the subject methods include obtaining the cellular sample from the donor.

According to certain embodiments, the cellular sample from the donor includes $0.001 \times 10^6$ to $2.0 \times 10^6$ cells. In certain aspects, the cellular sample from the donor includes $1 \times 10^6$ or fewer cells, such as $0.5 \times 10^6$ or fewer cells, $0.4 \times 10^6$ or fewer cells, $0.3 \times 10^6$ or fewer cells, $0.2 \times 10^6$ or fewer cells, $0.1 \times 10^6$ or fewer cells, or $0.5 \times 10^5$ or fewer cells. In certain aspects, the cellular sample from the donor includes from 25,000 to 200,000 cells.

By "recipient" is meant a source of the biological sample. The recipient may be different from the donor (e.g., where the DSAs may be alloantibodies), or the recipient and donor may be the same (e.g., where the DSAs may be autoantibodies). In certain aspects, the recipient (e.g., a human recipient) may be a candidate for receiving cells (e.g., blood cells), tissues (e.g., cornea, skin, bone, heart valve, tendon, femoral and/or saphenous veins, and the like), organs (e.g., a kidney, heart, pancreas, lung, liver, intestine, eye, and the like), and any combinations thereof, from the donor (e.g., to alleviate a medical condition) or may have already received cells, a tissue, or an organ from the donor. Recipients of interest include human recipients, non-human primate recipients, mammalian recipients, non-mammalian recipients, and any other recipient types of interest.

The "biological sample" from the recipient may be any biological sample from the recipient which includes or may include donor specific antibodies (DSAs). According to certain embodiments, the biological sample from the recipient is selected from serum, plasma, blood, saliva, tissue, and any combination thereof. In certain aspects, the biological sample is 100 µL or less of serum, plasma, blood, saliva, or any combination thereof, such as 90 µL or less, 80 µL or less, 70 µL or less, 60 µL or less, 50 µL or less, 40 µL or less, 30 µL or less, 20 µL or less, or 10 µL or less of serum, plasma, blood, saliva, or any combination thereof. According to one embodiment, the biological sample from the recipient is 30 µL or less of serum, plasma, blood, saliva, or any combination thereof. In certain aspects, the subject methods include obtaining the biological sample from the recipient.

Forming a mixture by combining a cellular sample from a donor with a biological sample from a recipient occurs under conditions sufficient for recipient immune antibodies (e.g., DSAs), if present, to bind to donor cell surface antigen (Ag) to form an immune antibody-Ag complex. According to certain embodiments, the recipient immune antibodies are alloantibodies. In other aspects, the recipient immune antibodies are autoantibodies. Conditions sufficient for recipient immune antibodies (e.g., DSAs), if present, to bind to donor cell surface antigen (Ag) may be provided by selection of a suitable buffer (e.g., PBS, TBS, or the like), detergents (e.g., Tween), protein (e.g., BSA), pH, temperature, duration and/or the like. Conditions useful to permit specific binding of antibodies to their target antigens are described, e.g., in Coligan, et al., eds., Current Protocols in Immunology, John Wiley & Sons, Inc., NY (1994-2013). In certain aspects, the cellular sample from the donor (e.g., $0.2 \times 10^6$ cells) and the biological sample from the recipient (e.g., 50 µL serum from the recipient) are incubated for about 20 minutes at room temperature in a suitable buffer to permit the recipient immune antibodies to bind to donor cell surface antigen. In certain aspects, the mixing, contacting and/or detecting steps are performed at room temperature.

In certain aspects, the donor specific antibody is actual donor specific antibody.

According to certain embodiments, the donor cell surface antigen is an HLA antigen, such that the donor specific antibodies are anti-HLA antibodies. In certain aspects, the donor specific antibodies are anti-HLA class I and/or anti-HLA class II antibodies. According to certain embodiments, the donor specific antibodies bind to a donor cell surface antigen selected from HLA-A, HLA-B, HLA-C, HLA- DRB1, HLA-DRB3, HLA-DRB4, HLA-DRB5, HLA-DQA, HLA-DQB, HLA-DPA, and HLA-DPB.

The donor specific antibodies, if present, may be complement fixing antibodies (CFAbs). In certain aspects, methods of the invention include not only determining the presence or absence of donor specific antibodies in the biological sample, but also include determining whether the DSAs are CFAbs or non-CFAbs. Identification of the DSAs as CFAbs may be performed, e.g., using a directly- or indirectly-labeled binding agent that specifically binds to CFAbs (and/or non-CFAbs). According to certain embodiments, the binding agent is an isolated complement component C1q. The C1q may be directly or indirectly labeled with a fluorescent label that is distinguishable from any other fluorescent labels in the complex. In certain aspects, the isolated C1q is conjugated to biotin ("Bio-C1q") and may be detected by addition of fluorescently-labeled streptavidin (e.g., R-phycoerythrin-conjugated streptavidin (SA-PE)). According to the above embodiments, the C1q protein binds to the Ag-Ab DSA if the DSA is a complement fixing antibody, and the directly or indirectly labeled C1q may be detected in the complex (along with the differentially detectably labeled antibody bound to the DSA) during the downstream detection step of the method (e.g., in a flow cytometer), indicating that the DSA is a CFAb.

Following forming the mixture, the mixture is contacted with beads that include an antibody that specifically binds the donor cell surface antigen (e.g., an HLA antigen) of the antibody-Ag complex. Depending on the donor cell surface antigen of interest, such beads may be commercially available. Otherwise, the desired type of bead (e.g., an agarose, latex, polystyrene, magnetic, or other type of bead) may be conjugated to an antibody that binds the antigen of interest using conjugation strategies known in the art. See, e.g., G. T. Hermanson, "Bioconjugate Techniques" Academic Press, 2nd Ed., 2008. Moreover, kits including reagents and instructions for conjugating an antibody of interest to a bead are commercially available (e.g., the Dynabeads® Antibody Coupling Kit (Life Technologies, Carlsbad, Calif.)). The beads may be microbeads having an average bead diameter of from 0.1 to 20 microns, such as from 0.5 to 10 microns, e.g., 5 microns or less (e.g., 2.5 to 5 microns). The contacting is typically carried out under conditions sufficient for the antibody included on the bead to specifically bind the donor cell surface antigen (e.g., an HLA antigen) to which the recipient immune antibody (e.g., a DSA) is already bound. Providing such conditions may include selection of a suitable buffer (e.g., PBS, TBS, or the like), detergent (e.g., Tween), protein (e.g., BSA), pH, temperature, duration and/or the like. Conditions useful to permit specific binding of antibodies to their target antigens are described, e.g., in Coligan, et al., eds., Current Protocols in Immunology, John Wiley & Sons, Inc., NY (1994-2013). Optionally, the mixture is washed between the mixing and contacting steps.

The contacting step results in the immune antibody-Ag complex including the donor cell surface antigen bound by: a recipient immune antibody (e.g., a DSA), if present; and the antibody present on the bead. A donor cell of the cellular sample is also associated with this complex by virtue of the donor cell surface antigen of the complex remaining on the surface of the donor cell. Following the contacting step, a detectably-labeled antibody that specifically binds the complex (e.g., the recipient immune antibody (e.g., the DSA) of the complex) is added under lysis conditions. Optionally, one or more wash steps are performed between the contacting step and the addition of the detectably labeled antibody under lysis conditions. The lysis conditions are sufficient to lyse the cells associated with the complexes, thereby freeing the complexes from the donor cells and facilitating downstream analysis of the complexes (e.g., by flow cytometry). In certain aspects, the lysis conditions include administering a lysis buffer that includes tracer, detergent, protease inhibitor, and BSA.

The detectably-labeled antibody and the lysis conditions may be provided by adding a "lysis mix" to the mixture after the contacting step, where the lysis mix includes the detectably labeled antibody in a lysis buffer. Any suitable lysis buffer may be used and may include one or more of Tris-HCl, EDTA, EGTA, SDS, deoxycholate, Triton X, NP-40, and/or any other desirable lysis buffer components. The lysis buffer is such that the immune antibody-Ag complex remains intact. The lysis buffer is non-denaturing according to certain aspects of the present disclosure. The immune antibody-Ag complex now includes the bead-associated antibody bound to the donor cell surface antigen, the recipient immune antibody (e.g., DSA), if present, bound to the donor cell surface antigen, and the detectably labeled antibody bound to the recipient immune antibody (e.g., DSA), if present. The detectable signals from the detectably labeled antibody of the complex may be measured and proportionally correlated with the amount of recipient immune antibody (e.g., DSA) in the biological sample from the recipient.

As set forth above, the methods of the present disclosure include detecting (e.g., quantitatively detecting) the presence or absence of the detectably-labeled antibody bound to the immune antibody-Ag complex to determine the presence or absence of donor specific antibodies in the biological sample from the recipient. The detection strategy employed may vary according to the types of detectable label(s) present on the detectably labeled antibody. Detectable labels that find use in practicing the subject methods include, but are not limited to, a fluorophore, a chromophore, an enzyme, a linker molecule, a biotin molecule, an electron donor, an electron acceptor, a dye, a metal, or a radionuclide.

According to certain embodiments, the detectably labeled antibody is fluorescently-labeled and includes a fluorophore selected from indocarbocyanine (C3), inodicarbocyanine (C5), Cy3, Cy3.5, Cy5, Cy5.5, Cy7, Texas Red, Pacific Blue, Oregon Green 488, Alexa fluor-355, Alexa Fluor 488, Alexa Fluor 532, Alexa Fluor 546, Alexa Fluor-555, Alexa Fluor 568, Alexa Fluor 594, Alexa Fluor 647, Alexa Fluor 660, Alexa Fluor 680, Alexa Fluor 700, JOE, Lissamine, Rhodamine Green, BODIPY, fluorescein isothiocyanate (FITC), carboxy-fluorescein (FAM), Allophycocyanin (APC), phycoerythrin (PE), rhodamine, dichlororhodamine (dRhodamine), carboxy tetramethylrhodamine (TAMRA), carboxy-X-rhodamine (ROX), LIZ, VIC, NED, PET, SYBR, PicoGreen, and RiboGreen.

When the detectably labeled antibody is fluorescently-labeled, the detecting may include detecting one or more fluorescence emissions. The fluorescence emission(s) may be detected in any useful format. In certain aspects, the detecting includes flowing the immune antibody-Ag complexes (which include a bead) through a flow cytometer.

When the detecting includes flowing the recipient immune antibody-Ag complexes through a flow cytometer, the flow cytometer is configured to detect and uniquely identify the complexes by exposing the complexes to excitation light and measuring the fluorescence of each complex in one or more detection channels, as desired. The excitation light may be from one or more light sources and may be either narrow or broadband. Examples of excitation light sources include lasers, light emitting diodes, and arc lamps.

Fluorescence emitted in detection channels used to identify the complexes may be measured following excitation with a single light source, or may be measured separately following excitation with distinct light sources. In certain aspects, the flow cytometer through which the mixture is flowed includes fluorescence excitation and detection capabilities such that the fluorescent label of the detectably labeled antibody, and any other optional fluorescent labels associated with other components of the complex are each detectable and distinguishable upon interrogation of the complexes by the flow cytometer.

Flow cytometers further include data acquisition, analysis and recording means, such as a computer, where multiple data channels record data from each detector for the light scatter and fluorescence emitted by each complex as it passes through the sensing region. The purpose of the analysis system is to classify and count complexes where each complex presents itself as a set of digitized parameter values. The flow cytometer may be set to trigger on a selected parameter in order to distinguish the complexes of interest from background and noise. "Trigger" refers to a preset threshold for detection of a parameter. It is typically used as a means for detecting passage of a complex through the laser beam. Detection of an event which exceeds the threshold for the selected parameter triggers acquisition of light scatter and fluorescence data for the complex. Data is not acquired for complexes or other components in the medium being assayed which cause a response below the threshold. The trigger parameter may be the detection of forward scattered light caused by passage of a complex through the light beam. The flow cytometer then detects and collects the light scatter and fluorescence data for the complex.

Flow cytometric analysis of the complexes, as described above, yields qualitative and quantitative information about the complexes. Where desired, the above analysis yields counts of the complexes of interest in the mixture. As such, the flow cytometric analysis provides data regarding the numbers of one or more different types of complexes in the mixture.

The mixing, contacting and detecting steps may be performed collectively in any convenient amount of time. According to certain embodiments, the methods of the present disclosure are performed in 12 hours or less, such as 11 hours or less, 10 hours or less, 9 hours or less, 8 hours or less, 7 hours or less, 6 hours or less, 5 hours or less, 4 hours or less, 3 hours or less, or 2 hours or less.

According to certain embodiments, methods of the present disclosure include generating a report indicating whether donor specific antibodies are present in the biological sample from the recipient. If DSAs are present, the report may include information regarding the amount of DSA in the biological sample from the recipient. The report may be generated by a computer, in which case the report is optionally displayed to an output device at a location remote to the computer.

In certain embodiments, methods of the present disclosure are used to detect DSAs that bind to donor HLA antigens (e.g., HLA class I and/or HLA class II antigens) present on cells in the cellular sample from the donor. According to one embodiment, a mixture is formed by combining a cellular sample that includes HLA antigen-containing donor cells with serum or plasma from the recipient such that any DSAs capable of specifically binding to the donor HLA may bind to the donor HLA. The resultant mixture containing the DSA-HLA complexes may be washed one or more times (e.g., three times) prior to the contacting step. According to this embodiment, the contacting step includes adding anti-HLA antibody-coated microbeads such that the anti-HLA antibodies attached to the beads bind to the constant regions of donor HLA class I and/or class II molecules on the surface of the donor cells. The resultant complex, which now includes capture beads bound to the donor HLA antigens, may be washed one or more times (e.g., three times) before proceeding with the method. According to this embodiment, fluorescently-labeled anti-IgG antibodies (e.g., PE-anti-IgG antibodies) are added under lysis conditions, such that the anti-IgG antibodies bind the DSA of the complex. Lysis of the donor cells facilitates separation of the complexes from other material present in the mixture. Next, fluorescence from the fluorescently-labeled anti-IgG antibodies may be detected, and optionally quantitated, to determine the presence (and optionally the amount/concentration) or absence of DSAs in the recipient serum or plasma which bind to donor HLAs. In certain aspects, the methods are used to interrogate the recipient serum or plasma for the presence or absence of DSAs that bind to HLA Class I and/or Class II, e.g., HLA-A, HLA-B, HLA-C, HLA-HLA-DRB1, HLA-DRB3, HLA-DRB4, HLA-DRB5, HLA-DQA, HLA-DQB, HLA-DPA, and HLA-DPB.

A method according to one embodiment of the present disclosure is schematically illustrated in FIG. 1. According to this embodiment, immune antibody-Ag complexes are detected by a flow cytometer or Luminex machine. In the reaction, donor cells are combined with recipient serum. Donor specific antibody (DSA), if present, specifically binds to the antigen (Ag) on donor cells to form a DSA-Ag complex. Under lysis conditions, the DSA-Ag complex is specifically captured by beads conjugated with antibody against the same Ag as in the DSA-Ag complex. The captured DSA-Ag is detected by a fluorescently-labeled secondary antibody through a flow cytometer or Luminex machine.

A method according to a second embodiment of the present disclosure is schematically illustrated in FIG. 2. According to this embodiment, immune antibody-Ag complexes are detected by an enzyme-linked immunosorbent assay (ELISA). In the reaction, donor cells are combined with recipient serum. Donor specific antibody (DSA), if present, specifically binds to the antigen (Ag) on donor cells to form a DSA-Ag complex. Upon lysis of the cell, the DSA-Ag complex is specifically captured on a substrate via an antibody against the same Ag as in the DSA-Ag complex. An enzyme linked secondary anti-IgG antibody binds to the DSA, and the DSA is detectable upon reaction of the enzyme and substrate. Variations of this approach (e.g., luminescence assays) are also provided by the present disclosure.

Systems

Also provided are systems for performing the methods of the present disclosure. Systems of the present disclosure include a sample fluid subsystem that includes a processor and a computer-readable medium operably coupled to the processor with stored programming thereon. When executed by the processor, the stored programming programs the processor to form a mixture by combining a cellular sample from a donor with a biological sample from a recipient under conditions sufficient for recipient immune antibodies, if present, to bind to donor cell surface antigen (Ag) to form an immune antibody-Ag complex. When executed by the processor, the stored programming also programs the processor to contact the mixture with beads comprising an antibody that specifically binds the immune antibody-Ag complex on a surface thereof, and add under lysis conditions a detectably labeled antibody that specifically binds the immune antibody-Ag complex. The subject systems also include a flow cytometer configured to assay the sample for the presence or absence of the detectably labeled antibody bound to the immune antibody-Ag complex to determine the presence or absence of donor specific antibodies. In certain aspects, the flow cytometer is fluidically coupled to the sample fluidic subsystem.

The processor may be any suitable processor for executing the stored programming. According to certain embodiments, the processor is programmed to cause the sample fluidic subsystem to wash the mixture before the subsystem contacts the mixture with the with beads comprising an antibody that specifically binds the immune antibody-Ag complex on a surface thereof. Alternatively, or additionally, the processor may be programmed to cause the sample fluidic subsystem to wash the mixture after the subsystem contacts the mixture with the beads comprising an antibody that specifically binds the immune antibody-Ag complex, but before the flow cytometer assays the sample for the presence or absence of detectable labels bound to the complexes.

The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. A computer readable storage medium may be any tangible medium that can contain, or store a program for use by or in connection with the sample fluidic subsystem of the systems of the present disclosure.

The cellular sample from the donor, the donor cell surface antigens, the biological sample from the recipient, the recipient immune antibodies (e.g., anti-HLA DSAs), the beads comprising an antibody that specifically binds the immune antibody-Ag complex on a surface thereof, the detectably labeled antibodies, the buffers, binding and lysis conditions, and the flow cytometer may be as described hereinabove with respect to the methods of the present disclosure.

The systems of the present disclosure may be configured to detect the presence or absence of DSAs in a convenient amount of time. According to certain embodiments, the subject systems are configured to detect the presence or absence of DSAs in a biological sample of the recipient in 12 hours or less, such as 11 hours or less, 10 hours or less, 9 hours or less, 8 hours or less, 7 hours or less, 6 hours or less, 5 hours or less, 4 hours or less, 3 hours or less, or 2 hours or less.

Kits

Kits which include one or more reagents useful for performing the methods of the present disclosure are also provided. According to one embodiment, provided is a kit that includes a plurality of beads comprising antibodies that specifically bind an immune antibody-Ag complex on a surface thereof, a detectably labeled antibody that specifically binds the immune antibody-Ag complex, and instructions for using the plurality of beads and the detectably labeled antibody to assay a cellular sample from a donor and a biological sample from a recipient to determine the presence or absence of donor specific antibodies in the biological sample. The subject kits may further include other useful components such as lysis buffer, control serum or plasma, a control cellular sample, and the like. The beads comprising an antibody that specifically binds an immune antibody-Ag complex on a surface thereof, and the detectably labeled antibody that specifically binds the immune antibody-Ag complex, may be as described hereinabove with respect to the methods of the present disclosure.

Reagents included in the subject kits may be provided in separate tubes, or two or more reagents may be provided in a single tube. According to one embodiment, the beads and detectably labeled antibodies are provided in separate tubes. In certain aspects, the detectably labeled antibody is provided in a lysis buffer.

According to one embodiment, instructions included in the subject kits are provided on a computer-readable medium which, when executed by a processor, programs the processor to assay a cellular sample from a donor and a biological sample from a recipient to determine the presence or absence of DSAs in the biological sample.

Utility

The subject methods, systems and kits find use in any application in which it is desirable to detect donor specific antibodies in a biological sample of a recipient. Recipients of interest include, but are not limited to, human recipients in need of, or having already received, an organ (e.g., kidney, liver, heart, etc.) or tissue transplant from an organ or tissue donor. Applications of interest include pre-transplantation risk assessment and/or post-transplantation monitoring based on detecting and/or quantifying the levels of DSAs in the biological sample of the recipient.

The methods of the present disclosure allow the distinction between antibodies reactive to the donor cells and antibodies reactive to the HLA molecules on the donor cells. Prior flow crossmatch technologies are deficient in that they are not capable of making this important distinction, where a positive flow crossmatch result might be completely irrelevant to antibody interactions with HLA.

The subject methods provide a platform which can be broadly used to develop many different DSA assays. Any type of biological sample from the recipient and any target cell of interest may be used to determine whether DSA is present or absent. Compared to existing approaches, the subject methods allow recipient antibodies to bind to donor antigens in their native configuration without any modifications and with high detection specificity and high throughput. Moreover, the methods may be completed in less time, and require fewer donor cells, than existing DSA detection approaches. Background signal caused by antibodies unrelated to the target antigen of interest is eliminated by virtue of specific antibody-mediated solid-phase capture of complexes that include DSAs bound to the antigen of interest.

EXAMPLES

As can be appreciated from the disclosure provided above, the present disclosure has a wide variety of applications. Accordingly, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Those of skill in the art will readily recognize a variety of noncritical parameters that could be changed or modified to yield essentially similar results. Efforts have been made to ensure accuracy with respect to numbers used (e.g. amounts, temperature, etc.) but some experimental errors and deviations should be accounted for.

Example 1: DSA-FM Testing Procedure

The following procedure may be used to practice one embodiment of the subject methods, termed donor specific antibody flow cytometric crossmatch ("DSA-FXM"). This example procedure involves simultaneous capture and labeling, and can be completed in 2 hours or less.

First, prepare a 96-well layout format to arrange the F×M samples to be tested. Second, dispense $0.2 \times 10^6$ (less than 250 μl in volume) donor cells in all pre-selected wells in a 96-well plate according the plate layout. Centrifuge at 2,000×g for 3 minutes. Flick the plate and blot twice on a stacked paper tower before turning the plate over. Resuspend the cells by gentle vortexing. Add 50 μl/well of each serum to the pre-selected wells according the plate layout. Gently vortex the plate and incubate in a RT incubator (22° C.) for 20 minutes. Prepare lysis mix (for each well, PE-anti-hIgG and lysis buffer in a total volume of 23 μl) during the incubation. After the incubation, add 250 μl of 3% HBSA to each well and spin the plate as before. Flick the plate and blot twice on a stacked paper tower before turning the plate over. Repeat the wash steps for an additional 2 times by adding 250 μl 3% HBSA for each wash.

Add 5 μl Capture Beads Mix to each well at the last wash ($3^{rd}$ wash), and wash again as before using 250 μl 3% HBSA. Add 23 μl lysis mix (cell lysis buffer and fluorescence antibody) to each well and gently vortex the plate. Cover the plate with a piece of foil and incubate the plate in the dark with gentle shaking for 30 minutes. Prepare DSA-FXM wash buffer during the incubation as follows: to make 10 ml DSA-FXM wash buffer, add 0.5 ml detergent to 9.5 ml 1×TBS wash buffer and mix by inverting the tube five times.

Wash twice by adding 250 μl DSA-FXM wash buffer to each well and washing as before. Add 250 μl DSA-FXM wash buffer and wash as before. Resuspend the beads in each well with 200 μl Flow Fixative and gently vortex the plate. Place the plate onto a flow cytometer and acquire the beads. Experimental results are shown in FIG. 3, FIGS. 5-9, FIGS. 11-14, and FIG. 16.

Figure 3:
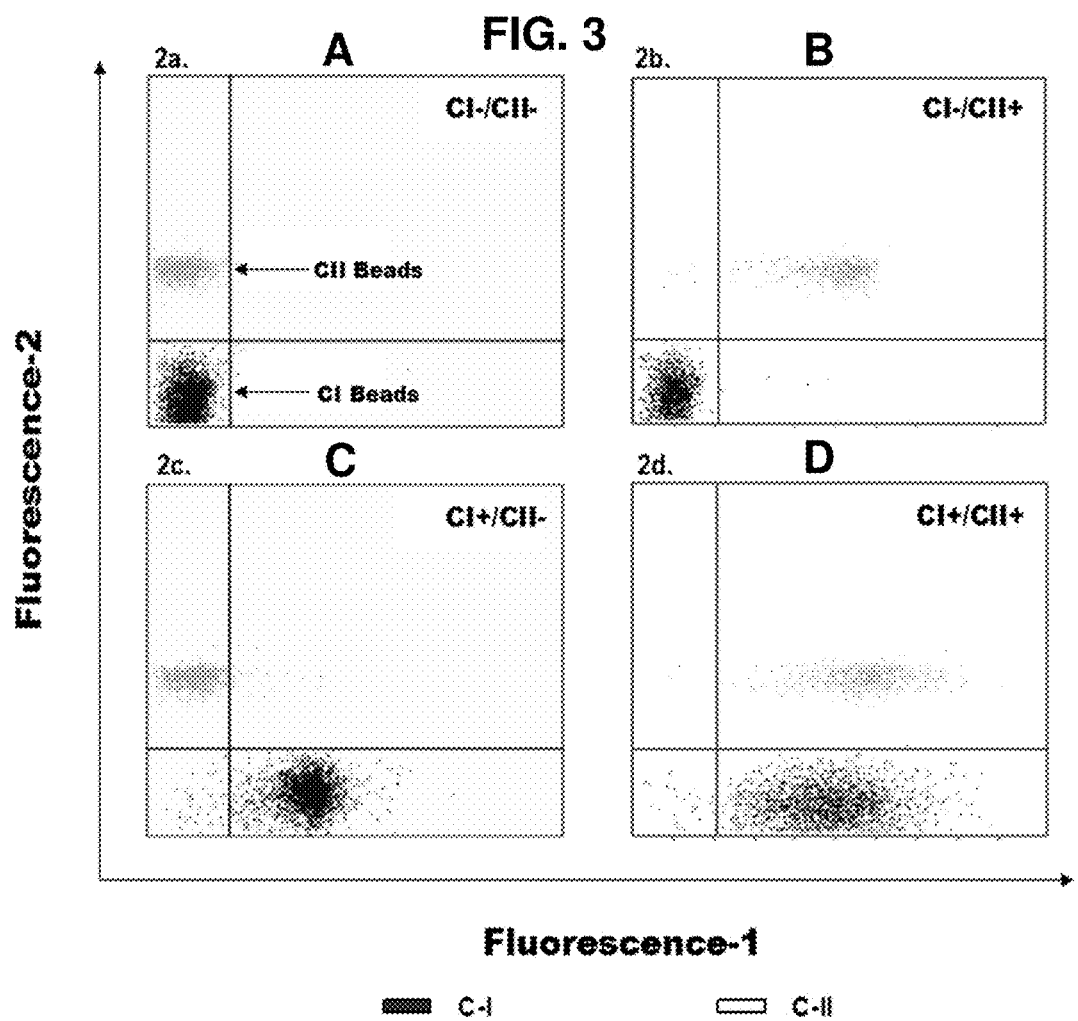
FIG. 3 shows results of a DSA-FXM experiment involving simultaneous capture and labeling of DSAs. Four samples were tested by DSA-FXM using HLA-Class I and Class II beads distinguished by the internal fluorescence ID of each bead. Increasing fluorescence (positive signal) due to HLA specific antibody is shown on the X axis.

For the experiment shown in FIG. 3, four samples were tested by DSA-FXM (the simultaneous capture and labeling embodiment) and HLA-Class I and Class II beads were distinguished by the fluorescence ID on each bead. Increasing fluorescence (positive signal) due to HLA specific antibody is shown on the X axis (FL1 channel). FIG. 3, panel A: both HLA-Class I (C-I) and Class II (C-II) donor specific antibody (DSA) were negative (CI−/CII−); FIG. 3, panel B: only C-II DSA was positive (CI−/CII+); FIG. 3, panel C: only C-I DSA was positive (CI+/CII−); and FIG. 3, panel D: both CI and C-II DSAs were positive (CI+/CII+).

Figure 5:
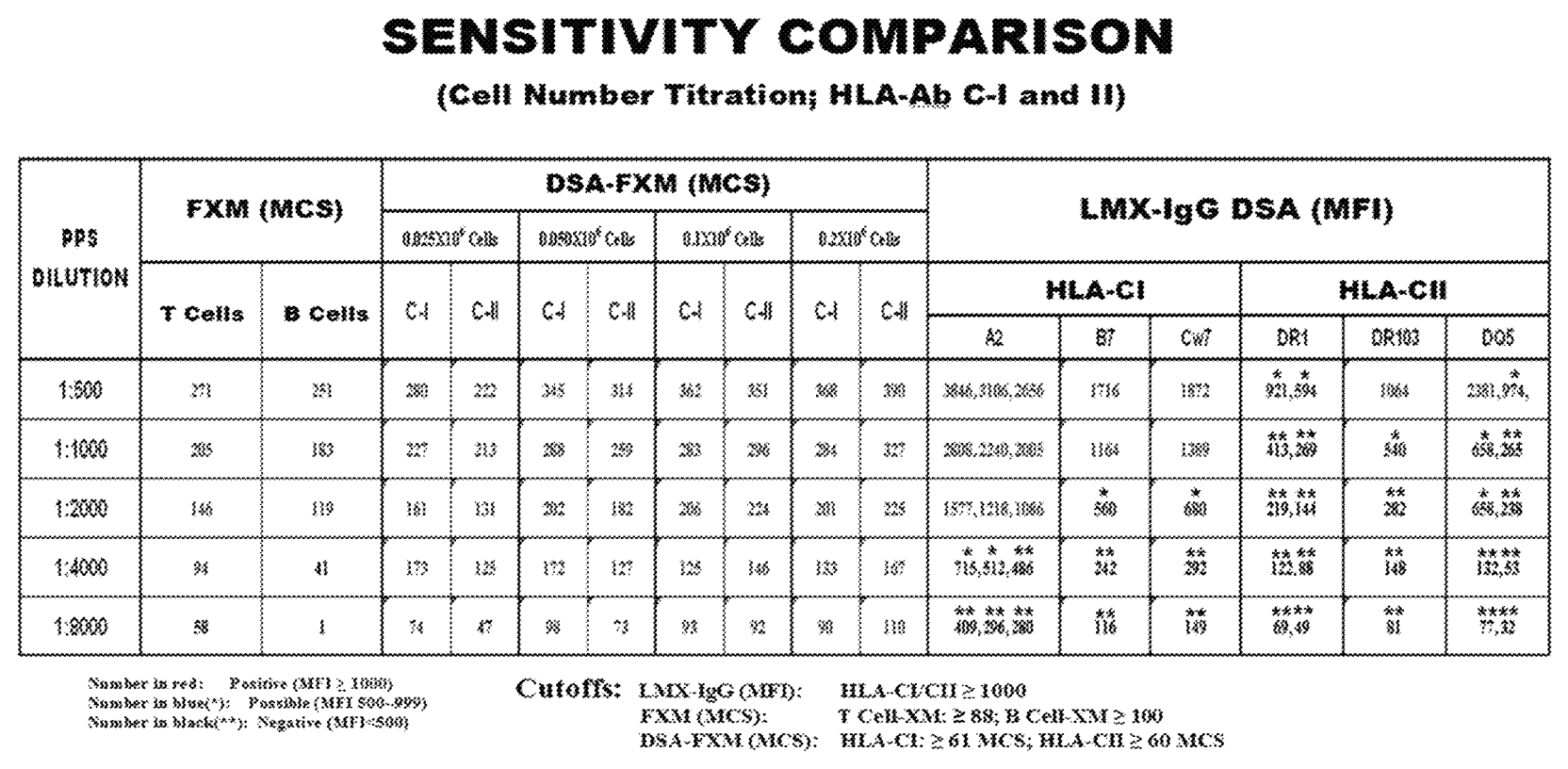

As shown in FIG. 5, a pool of HLA-Ab positive sera (PPS) in different dilutions was tested against various cell numbers by FXM, DSA-FXM, and LMX-IgG. The results show DSA-FXM is the most sensitive method for detecting DSA and uses many fewer cells (e.g. DSA can be detected with as few as 25,000 cells) when compared with standard methods. LMX-IgG defines the HLA specificities contained in the PPS serum on a Luminex platform using single antigen beads and the values shown are the mean fluorescence intensities (MFI).

As shown in FIG. 6, 23 external proficiency CAP samples (the College of American Pathologists) were tested by DSA-FXM simultaneously with the blinded challenge and in parallel with the regular flow crossmatch (FXM) and standard Luminex antibody screening on single antigen beads (LMX-IgG). The donor specific antibodies (DSAs) of HLA-class I (C-I) and/or HLA-II (C-II) were identified and most DSAs were further confirmed by LMX-IgG. Some extra DSA with low MCS were only detected with the more sensitive DSA-FXM method. External proficiency samples are sera and cells with known specificities. The specificities of the sera are blinded to the participants until all results are received from all participating centers. The data presented in FIG. 7 indicates that seven HLA-DQ DSA positive samples were identified by LMX-IgG and confirmed by DSA-FXM. As shown in FIG. 8, six HLA-DP DSA positive samples were identified by LMX-IgG and confirmed by DSA-FXM. As shown in FIG. 9, three HLA-C DSA positive samples were identified by LMX-IgG and confirmed by DSA-FXM.

Figure 11:
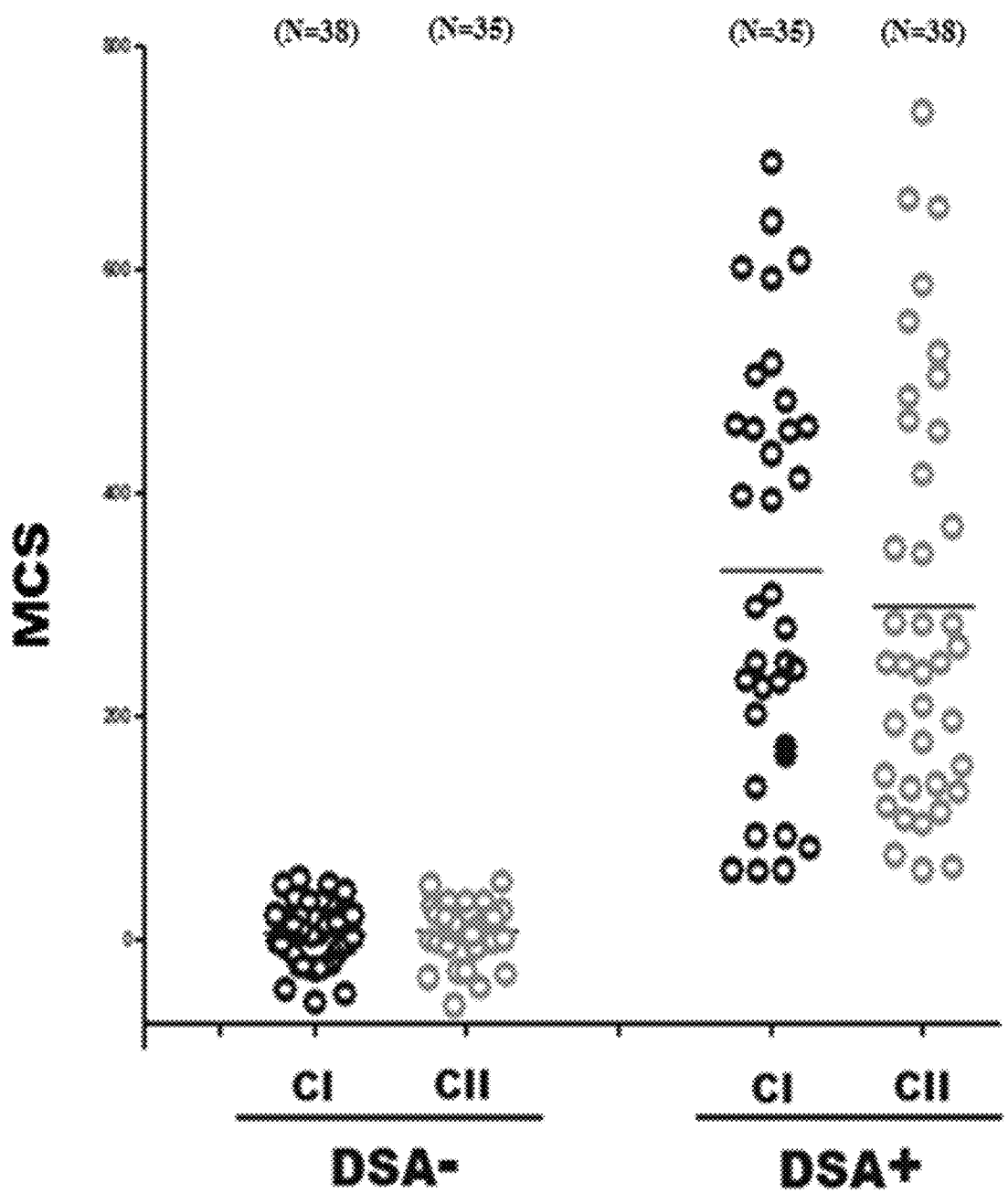
FIG. 11 provides results of 117 separate DSA-FXM tests with known class I and class II DSA reactivity or lack thereof, showing mutually exclusive patterns of reactivity correlated with the known DSA profiles.

As shown in FIG. 11, a collection of 117 sera including HLA typing reagents, negative controls, and clinical samples were tested whose DSA specificities were known from LMX-IgG SAB testing. Exclusive positive or negative reactions were obtained. When the results of the DSA-FXM were compared to the FXM and LMX-IgG SAB results, DSA-FXM had superior sensitivity for class I (FIG. 12) and class II (FIG. 13) than either of the other tests. FIG. 14, Panels A and B gives the overall correlation for 95 class I and 100 class II DSAs, respectively. FIG. 14, Panel C summarizes the sensitivity and specificity of the DSA-FXM compared to the LMX-IgG SAB assay. As shown in FIG. 14, Panel D, the reduced specificity obtained in the FIG. 14, Panel C comparison is due to false positive reactions in the LMX-IgG SAB assay and not to false negative reactions in the DSA-FXM assay.

Figure 15:
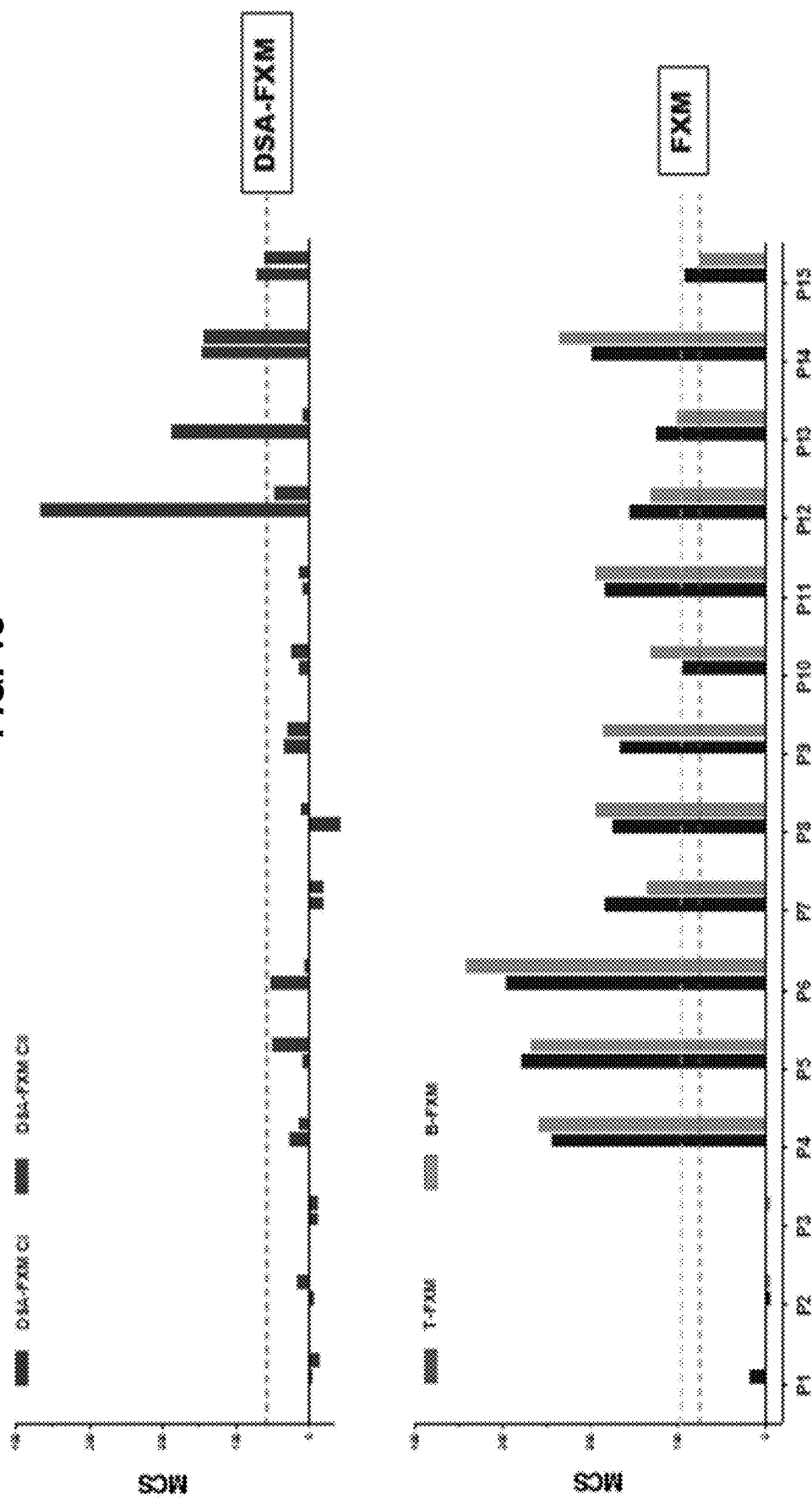
FIG. 15 shows a comparison of FXM and DSA-FXM on 15 patients, 12 of whom had autoantibody by FXM to antigens of unknown specificity (lower panel). Four of these patients (P12-P-15) had autoantibody directed to HLA as determined by DSA-FXM (upper panel)

As shown in FIG. 15, the T and B cell FXM assays yield non-specific (i.e., not due to HLA, target unknown) positive results in the presence of autoantibodies, whereas the DSA-FXM clearly distinguishes autoantibodies to HLA and discriminates whether the autoantibodies are to class I or class II.

As shown in FIG. 16, the DSA-FXM is able to distinguish flow cytometry results due to class I and/or class II alloantibody as well as to autoantibody which the current FXM method in general use cannot do. Similar results seen with the FXM (e.g., Cases 1 and 3 or 2 and 4) have completely different explanations and interpretations when tested by DSA-FXM. The DSA-FXM can be correlated with the specific class I and/or II DSA profiles obtained by LMX-IgG SAB to give a prognosis for risk of rejection pre- or post-transplant, whereas the FXM results cannot.

As shown in FIG. 17 for class I (Panel A) and class II (Panel B), the DSA-FXM is able to show inhibition of class specific DSA by IVIG treatment as compared to buffer. This parallels what is seen in vivo before and after IVIG infusion.

As shown in FIG. 18 for class I (Panel A) and class II (panel B), DSA specific sera show a dose-dependent inhibition by IVIG which also predicts in vivo efficacy.

As shown in FIG. 1, FXM and DSA-FXM were performed using serial samples from a kidney candidate undergoing IVIG desensitization treatment to prospectively lower/abrogate DSA to an identified potential living donor. FXM results show increased MCS values (i.e., became more positive) due to an artifact of IVIG infusion. The artifact is due to the second step antibody (anti-human IgG) which is used as the signal in the assay. Because all of the IVIG product is purified IgG, FXM results show false positive increases due to the IVIG, not to the DSA. Rituxan (therapeutic anti-CD20, a marker of B cells) also increases MCS values in the B cell FXM because of the CD20 on the B cell surface. Although this is not artifact, the FXM is designed to detect HLA antibody, not native cell specific targets. DSA-FXM results, in contrast, show inhibition (efficacy) of the IVIG and MCS values in the range acceptable for transplant even in the presence of the therapeutic (anti-CD20) antibodies.

Result Calculations

Use a DSA-FXM Analysis Worksheet to record and perform the calculations. Determine the Median Channel Shift (MCS) for Patient Sera & Positive controls. For calculation of MCS: MCS=Median Channel Value (MCV) of the patient sera (or Pos controls) minus Median Channel Value (MCV) of the Neg controls. Record the result as MCS on the worksheet and computer. Make a report according to the FXM cutoff to define a Negative or Positive DSA-FXM.

Results and Interpretation

The cutoffs for FXM were determined by the results (MCS) from pre-tested AB male sera (usually about 20) against 5 different sources of target cells (fresh/frozen PBMC, frozen lymph node, and frozen spleen cells). MCS for each tested AB serum was calculated by subtracting negative control MCV from AB serum MCV; and means of DSA-FXM MCS were calculated from all MCSs obtained (N=138). The criteria of DSA-FXM cutoffs were set as follows: MCS values<AB neg MCS+3 SD were interpreted as "Negative"; MCS values >=AB neg MCS+3SD were interpreted as "Positive". HLA-I DSA-FXM Positive: MCS >=61. HLA-II DSA-FXM Positive: MCS >=60.

Materials and Methods

For the FXM procedure, distribute $0.1 \times 10^6$ PBMC cells into each well in a 96-well plate and centrifuge at 1,300×g for 3 minutes. Flick the plate to remove the supernatant; resuspend the cells in 50 µl test serum and incubate in a RT incubator (22° C.) for 20 minutes. After the incubation, wash the cells four times with 250 µl of 3% HBSA each time. Add 100 µl detecting reagent mix containing 0.5 µg of FITC-anti human IgG (Jackson ImmunoResearch Laboratories, Inc.; West Grove, Pa., USA), 0.2 µg PerCP-CD3 and PE-CD19 (BD Biosciences, San Jose, Calif., USA). After an additional 30 minute incubation at room temperature, wash cells twice with 250 µl of 3% HBSA each time and resuspend in 200 µl 0.2% paraformaldehyde in PBS. Acquire cells on BD FACSCanto II Flow Cytometer (BD Biosciences, San Jose, Calif., USA). The acquired data are analyzed by BD FACSDiva™ software.

For the LMX-IgG procedure, experiments were performed according to the manufacturer's instructions (One Lambda, Canoga Park, Calif., USA). The result shows that both HLA class I and II DSA are detected by DSA-FXM in various conditions (FIG. 5).

Example 2: DSA-FXM Testing

The following procedure may be alternatively used to practice one embodiment of the subject methods, termed donor specific antibody flow cytometric crossmatch ("DSA-FXM"). This example procedure involves sequential capture and labeling.

First, prepare a 96-well layout format to arrange the FXM setting. Second, dispense $0.2 \times 10^6$ (less than 250 µl in volume) donor cells in all pre-selected wells in a 96-well plate according the plate layout. Centrifuge at 2,000×g for 3 minutes. Flick the plate to remove supernatant. Gently vortex the plate and add 50 µl/well of each serum to the pre-selected wells according the plate layout. Gently vortex the plate and incubate in a RT incubator (22° C.) for 20 minutes. After the incubation, add 250 µl of 3% HBSA to each well and spin the plate as before. Flick the plate and blot twice on a stacked paper tower before turning the plate over. Repeat the wash steps for an additional 2 times by adding 250 µl 3% HBSA for each wash.

Figure 4:
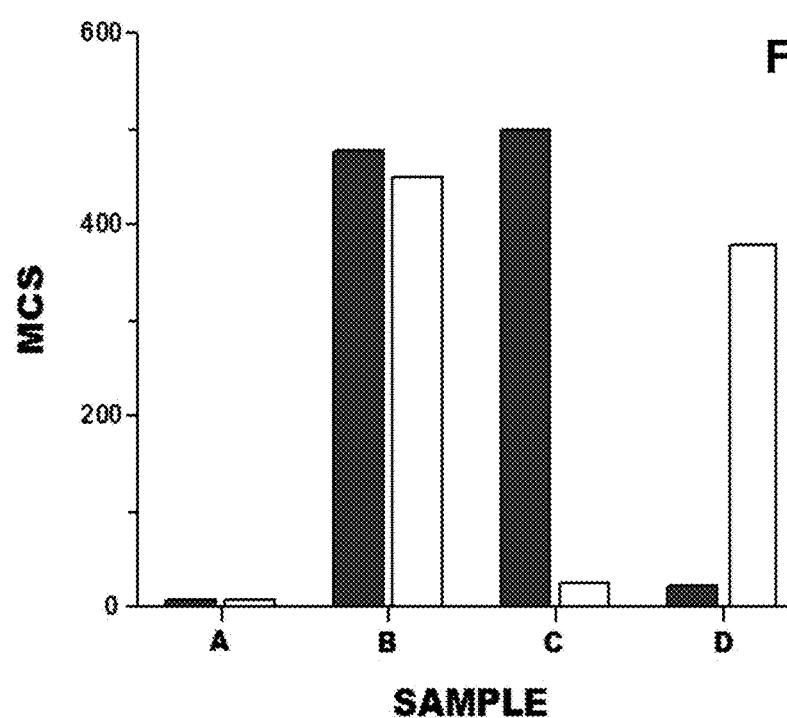
FIG. 4 shows results of a DSA-FXM experiment involving sequential capture and labeling of DSAs. A negative AB serum (Sample A) and three positive sera (Samples B, C and D) were tested by DSA-FXM. Sample A: both C-I and C-II DSA negative; Sample B: both C-I and C-II DSA positive; Sample C: only C-I DSA positive and C-II DSA negative; Sample D: only C-II DSA positive and C-I DSA negative.

Add 5 µl Capture Beads Mix containing HLA-class I and II capture beads to each well at the last wash (3rd wash), and wash again as before using 250 µl 3% HBSA. Add 23 µl cell lysis buffer to each well and gently vortex the plate. Cover the plate with a piece of foil and incubate the plate in the dark with gentle shaking for 30 minutes. Wash the beads twice with 250 µl each DSA-FXM wash buffer as before. Resuspend the beads with 100 ul of Fluorescent anti-IgG in wash buffer and incubate the plate at RT for an additional 30 minutes. Wash the beads twice with 250 µl each DSA-FXM wash buffer as before and resuspend the beads in each well with 200 µl Flow Fixative and gently vortex the plate. Place the plate onto a flow cytometer and acquire the beads. FXM and LMX-IgG procedures were carried out as described above. The experimental results are shown in FIG. 4. As shown in FIG. 4, A negative AB serum (Sample A) and three positive sera (Samples B, C and D) were tested by DSA-FXM (sequential capture and labeling). Sample A: both C-I and C-II DSA negative; Sample B: both C-I and C-II DSA positive; Sample C: only C-I DSA positive and C-II DSA negative; Sample D: only C-II DSA positive and C-I DSA negative.

Example 3: DSA-FXM Testing

The following procedure may be alternatively used to practice one embodiment of the subject methods, termed donor specific antibody flow cytometric crossmatch ("DSA-FXM"). This example procedure involves sequential capture and labeling.

First, prepare a 96-well layout format to arrange the FXM setting. Second, dispense $0.2 \times 10^6$ (less than 250 µl in volume) donor cells in all pre-selected wells in a 96-well plate according the plate layout. Centrifuge at 2,000×g for 3 minutes. Flick the plate to remove supernatant. Gently vortex the plate and add 50 µl/well of each serum to the pre-selected wells according the plate layout. Gently vortex the plate and incubate in a RT incubator (22° C.) for 20 minutes. After the incubation, add 250 µl of 3% HBSA to each well and spin the plate as before. Flick the plate and blot twice on a stacked paper tower before turning the plate over. Repeat the wash steps for an additional 2 times by adding 250 µl 3% HBSA for each wash.

Figure 10:
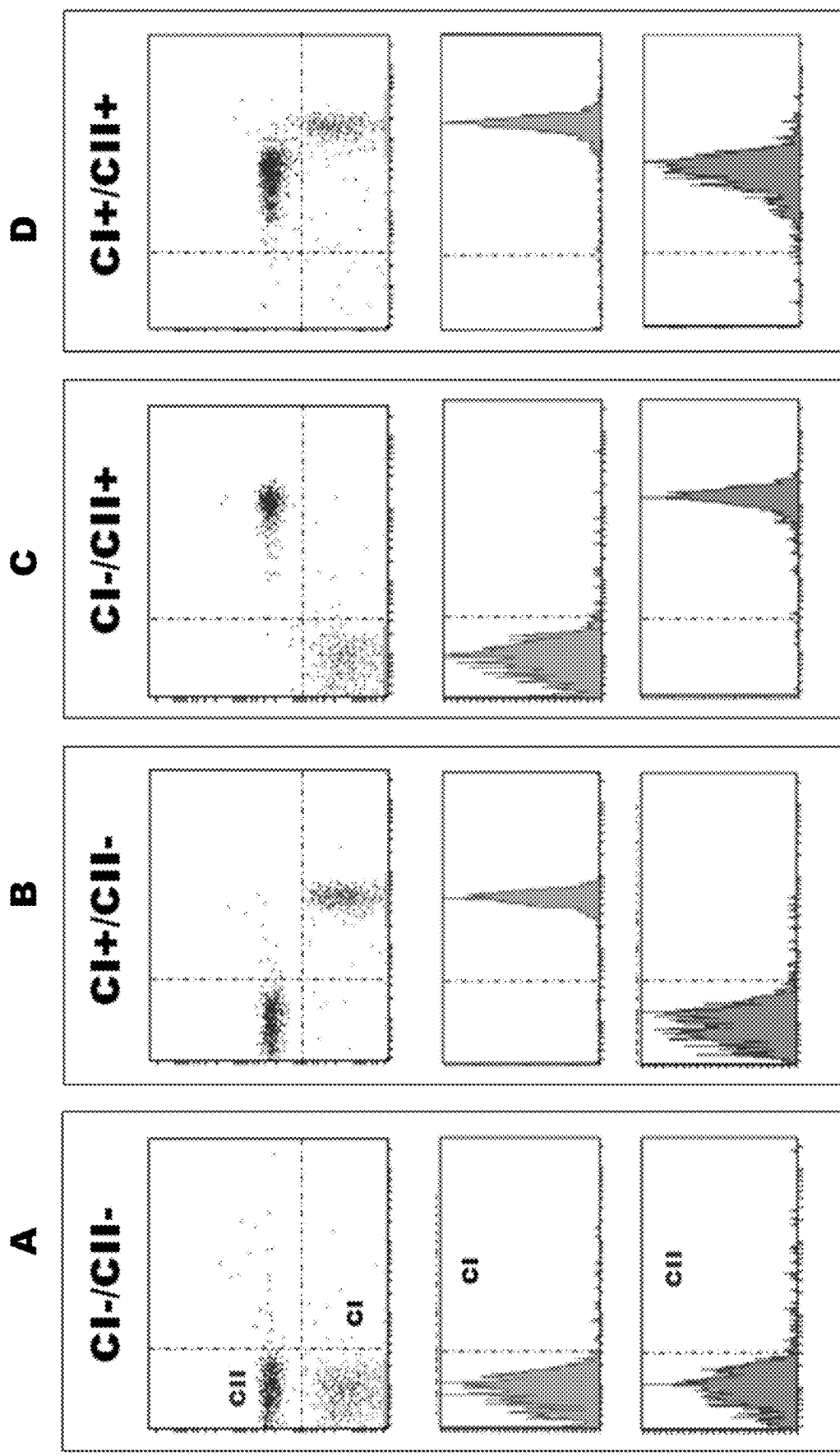
FIG. 10 shows experimental results from a DSA-FXM testing procedure. Panel A: both HLA-Class I (C-I) and Class II (C-II) donor specific antibody (DSA) were negative (CI−/CII−); Panel B: only C-I DSA was positive (CI+/CII−); Panel C: only C-II DSA was positive (CI−/CII+); and Panel D: both CI and C-II DSAs were positive (CI+/CII+).

Add 100 µl of Fluorescent anti-IgG to resuspend the cells and cover the plate with a piece of foil; and incubate the plate in the dark with gentle shaking for 30 minutes. Wash the cells twice with 250 µl each DSA-FXM wash buffer as before. Resuspend the cells in 25 µl lysis buffer and add 5 µl Capture Beads Mix containing HLA-class I and II capture beads to each well. Incubate the plate at RT for an additional 30 minutes. Wash the beads twice with 250 µl each DSA-FXM wash buffer as before and resuspend the beads in each well with 200 µl Flow Fixative and gently vortex the plate. Place the plate onto a flow cytometer and acquire the beads. FXM and LMX-IgG procedures were carried out as described above. The experimental results are shown in FIG. 10 and FIG. 11: FIG. 10, Panel A: both HLA-Class I (C-I) and Class II (C-II) donor specific antibody (DSA) were negative (CI−/CII−); FIG. 10, Panel B: only C-I DSA was positive (CI+/CII−); FIG. 10, Panel C: only C-II DSA was positive (CI−/CII+); and FIG. 10, Panel D: both CI and C-II DSAs were positive (CI+/CII+).

Example 4: Auto-DSA-FXM Testing

Autologous sera from 15 recipients were tested against the recipients' own PBMC cells by FXM in parallel with the DSA-FXM procedure described in Example 1. The experimental results are shown in FIG. 15: of 15 auto cross-matches, 3 were negative and 4 were positive by both DSA-FXM and FXM; 8 were only positive by FXM and proved that the DSAs detected by FXM were not DSAs against HLA antigens.

Example 5: Intravenous Immunoglobulin (IVIG) Desensitization DSA-FXM Testing

Figure 19:
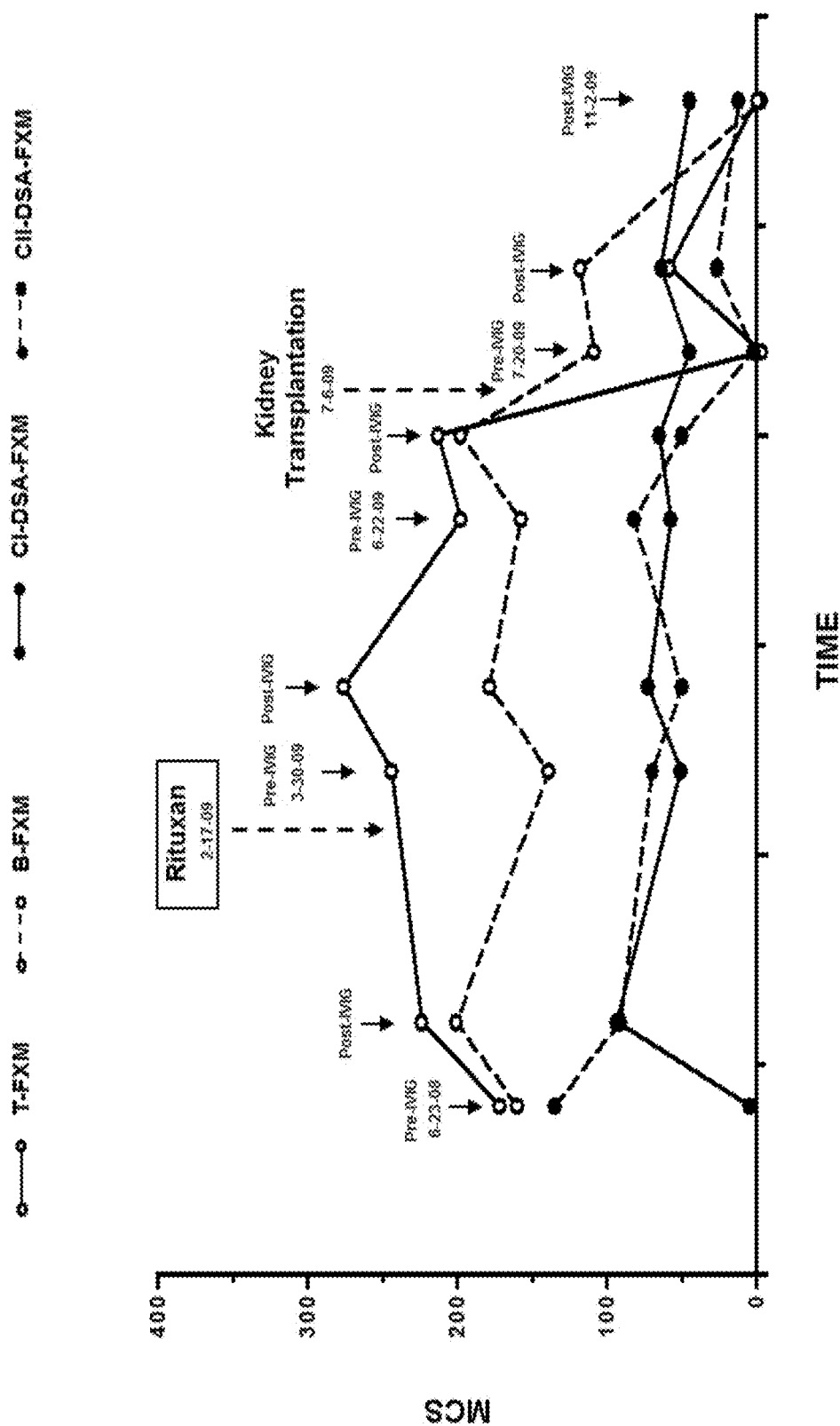
FIG. 19 shows FXM and DSA-FXM results on serial samples from a kidney candidate undergoing IVIG desensitization treatment to prospectively lower/abrogate DSA to an identified potential living donor. FXM results show increased MCS values due to IVIG and Rituxan (therapeutic anti-CD20, a marker of B cells) while DSA-FXM results show inhibition (efficacy) of the IVIG and MCS values in the range acceptable for transplant even in the presence of the therapeutic antibodies.

The inhibition effect of IVIG on HLA-DSA was evaluated by DSA-FXM testing procedure described in Example 1. Experimental results are shown in FIGS. 17-19.

For the experiment shown in FIG. 17, two HLA DSA positive sera were spiked with 5% IVIG and tested in vitro by DSA-FXM. The inhibition effect of IVIG on both HLA class I and II DSA was measurable.

As shown in FIG. 18, a positive DSA serum in different dilutions was spiked with 5% IVIG and tested by DSA-FXM. The result showed that IVIG had a dose-dependent inhibition on both HLA class I and II DSAs.

A series of samples from a kidney candidate under IVIG desensitization treatment were tested against a potential (but incompatible) living donor's cells by both DSA-FXM and FXM. As shown in FIG. 19, the inhibition effect of IVIG on HLA-DSA was observed by DSA-FXM but could not be seen by FXM. Rituxan (therapeutic anti-CD20) had no interference on the test results by DSA-FXM testing.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A kit for use in a method for determining the presence or absence of donor-specific antibodies in a biological sample from a recipient, the kit comprising:
   a plurality of beads comprising capture antibodies attached to a surface thereof that specifically bind a donor cell surface antigen (Ag) in a complex comprising the donor cell surface Ag bound to a recipient immune antibody;
   a lysis buffer; and
   a detectably-labelled antibody, wherein the detectably-labelled antibody specifically binds the recipient immune antibody complex under lysis conditions.

2. The kit according to claim 1, wherein the detectably-labelled antibody comprises a detectable label attached to an antibody or antigen binding fragment thereof.

3. The kit according to claim 2, wherein the detectable label comprises a fluorophore selected from the group consisting of: indocarbocyanine (C3), indodicarbocyanine (C5), Cy3, Cy3.5, Cy5, Cy5.5, Cy7, Texas Red, Pacific Blue, Oregon Green 488, Alexa fluor-355, Alexa Fluor 488, Alexa Fluor 532, Alexa Fluor 546, Alexa Fluor-555, Alexa Fluor 568, Alexa Fluor 594, Alexa Fluor 647, Alexa Fluor 660, Alexa Fluor 680, Alexa Fluor 700, JOE, Lissamine, Rhodamine Green, BODIPY, fluorescein isothiocyanate (FITC), carboxy-fluorescein (FAM), Allophycocyanin (APC), phycoerythrin (PE), rhodamine, dichlororhodamine (dRhodamine), carboxy tetramethylrhodamine (TAMRA), carboxy-X-rhodamine (ROX), PicoGreen, and RiboGreen.

4. The kit according to claim 1, wherein the average bead diameter is less than 5 microns.

5. The kit according to claim 1, wherein the average bead diameter is between 2.5 to 5 microns.

6. The kit according to claim 1, wherein the beads are agarose beads.

7. The kit according to claim 1, wherein the beads are latex beads.

8. The kit according to claim 1, wherein the beads are magnetic beads.

9. The kit according to claim 1, wherein the beads are polystyrene beads.

10. The kit according to claim 1, wherein the lysis buffer includes one or more of Tris-hydrochloride (HCl), Ethylenediaminetetraacetic acid (EDTA), Ethylene glycol-bis(2-aminoethylether)-N,N,N',N'-tetraacetic acid (EGTA), sodium dodecyl sulfate (SDS), and deoxycholate.

11. The kit according to claim 1, wherein the lysis buffer comprises the detectably labelled antibody.

\* \* \* \* \*